(12) United States Patent
Allbritton et al.

(10) Patent No.: US 7,236,888 B2
(45) Date of Patent: *Jun. 26, 2007

(54) METHOD TO MEASURE THE ACTIVATION STATE OF SIGNALING PATHWAYS IN CELLS

(75) Inventors: Nancy Allbritton, Irvine, CA (US); Christopher Sims, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/990,413

(22) Filed: Nov. 21, 2001

(65) Prior Publication Data

US 2002/0127604 A1 Sep. 12, 2002

Related U.S. Application Data

(63) Continuation-in-part of application No. 09/358,504, filed on Jul. 21, 1999, now Pat. No. 6,335,201, which is a continuation-in-part of application No. 09/036,706, filed on Mar. 6, 1998, now Pat. No. 6,156,576.

(60) Provisional application No. 60/252,861, filed on Nov. 22, 2000.

(51) Int. Cl.
*G06F 19/00* (2006.01)
*C12Q 1/25* (2006.01)

(52) U.S. Cl. .......................... 702/19; 435/4
(58) Field of Classification Search ................ 435/7.1; 500/350

See application file for complete search history.

(56) References Cited

U.S. PATENT DOCUMENTS 5,258,289 A 11/1993 Davis et al.
5,639,656 A * 6/1997 Wright, Jr. ................ 435/344.1
5,929,041 A * 7/1999 Magal .......................... 514/44
5,958,703 A 9/1999 Dower et al.
6,156,576 A 12/2000 Allbritton et al.

FOREIGN PATENT DOCUMENTS

| WO | WO99/45372 | 9/1999 |
|----|------------|--------|
| WO | WO00/23615 | 4/2000 |
| WO | WO00/50872 | 8/2000 |
| WO | WO01/07910 | 2/2001 |
| WO | WO 01/44269 A2 | 6/2001 |

OTHER PUBLICATIONS

Day et al., Biotechniques, vol. 25, pp. 848-850, 1998.*
Sims et al., Journal of Biological Chemistry, vol. 273; pp. 4052-4058, 1998.*
Dictionary.com, pp. 1-3, 2003.*
Lee et al. Localized measurement of kinase activation in oocytes of Xenopus laevis. Nature Biotechnology vol. 17, pp. 759-762 (1999).*
Luzzi, V., C.L. Lee, and N.L. Allbritton. 1997. Localized sampling of cytoplasm from Xenopus oocytes for capillary electrophoresis. Analytical Chemistry. 69:4761-7.

* cited by examiner

*Primary Examiner*—John S. Brusca
(74) *Attorney, Agent, or Firm*—Evan Law Group LLC

(57) ABSTRACT

The activity of multiple proteins in a single living cell, portion of a cell or in a group of cells is simultaneously measured by introducing reporter molecules into the cell(s) or a portion thereof, chemically modifying the reporter(s) by the enzyme of interest, terminating the modification reactions, removing the reporter(s) and modified reporter(s), and determining the amount of enzyme activity present by measuring or comparing the amount of reporter(s) and modified reporter(s) present. By performing a series of experiments at different time points, conditions, and varieties of cell types, a database is developed for molecular cellular mechanisms in health and disease states. By exposing cells to a variety of compounds data for drug development and screening is provided.

33 Claims, 33 Drawing Sheets

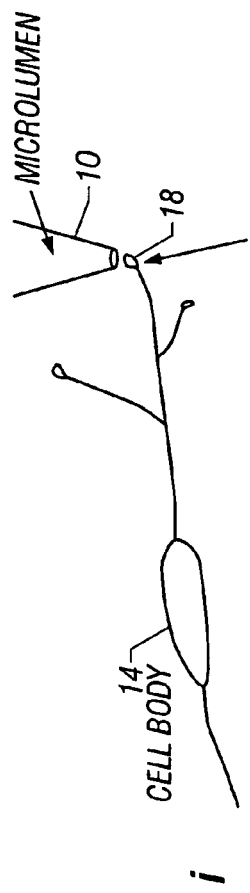
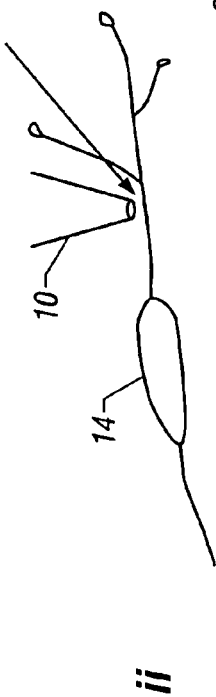
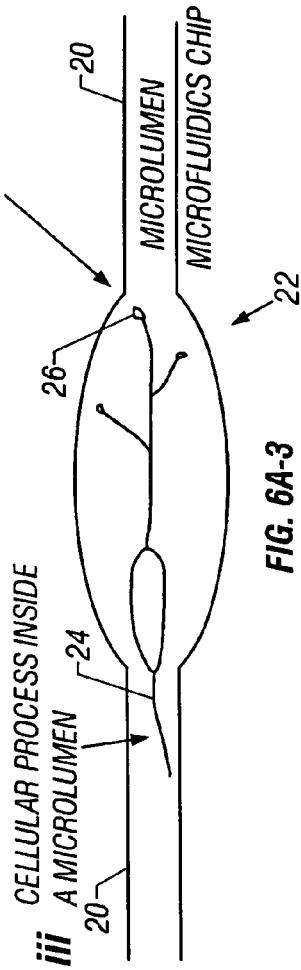
FIG. 6A-1
FIG. 6A-2
FIG. 6A-3

OR

*Microinjection*

*Simple Lipid-Assisted Microinjection*

*Optoinjection*

COMPUTER-CONTROL OF MICROLUMEN ALIGNMENT OVER CELLS, LYSIS, AND/OR OTHER STEPS.

TABLE I

INFLUENCE OF THE INTRACELLULAR ENVIRONMENT

| CELLULAR PROPERTY | IS IT THE SAME AFTER REMOVAL FROM THE CELL? |
| --- | --- |
| 1. DNA, RNA (SEQUENCE, QUANTITY) | YES |
| 2. PROTEIN (IDENTITY, CONC.) | LIKELY |
| 2. ACTIVITY | USUALLY NOT |

FIG. 26A-1

TABLE II

CELLULAR PROPERTIES ARE DISTINGUISHED BY THEIR TIMESCALES

| | |
| --- | --- |
| DNA & RNA "GENOMICS" | MINUTES - YEARS |
| PROTEIN "PROTEOMICS" | SECONDS - HOURS |
| ACTIVITY "SIGNALING" | MILLISECONDS - SECONDS |

FIG. 26A-2

TABLE III

*A SAMPLING OF
AVAILABLE TECHNOLOGIES*

| FIELD | PROPERTY | TECHNOLOGIES |
|---|---|---|
| 1. GENOMICS | DNA, RNA | DNA ARRAYS |
| 2. PROTEOMICS | PROTEIN IDENTITY & CONC. | PROTEIN GELS/ARRAYS MASS SPEC. |
| 3. SIGNALING | ACTIVITY | GFP - BASED METHODS CRITICAL NEED |

*FIG. 26A-3*

METHOD TO MEASURE THE ACTIVATION STATE OF SIGNALING PATHWAYS IN CELLS

RELATED APPLICATIONS

This application is related to and claims priority from U.S. Provisional Patent Application Ser. No. 60/252,861, filed Nov. 22, 2000; this application is also a continuation-in-part application of application Ser. No. 09/358,504 filed Jul. 21, 1999 and entitled "Method and Apparatus for Detecting Enzymatic Activity Using Molecules that Change Electrophoretic Mobility", now issued as U.S. Pat. No. 6,335,201 (2002), which was in turn a continuation-in-part application of application Ser. No. 09/036,706 filed Mar. 6, 1998, and entitled "Fast Controllable Laser Lysis of Cells for Analysis" now issued as U.S. Pat. No. 6,156,576 (2000).

BACKGROUND OF THE INVENTION

1 Field of the Invention

This invention relates to the areas of the biochemical and chemical analysis of molecules in cells, and in particular to an assay and method for measuring the activation of internal chemical activity of a plurality of proteins in a single cell, a population of cells, or portion of a cell.

2. Description of the Prior Art

All cells are composed of complex networks of proteins that allow them to respond to the environment and to go about the business of life (FIG. 1-2). At any given time all of the proteins in a cell are not active. The determination of which proteins are active in a living cell and how networks of proteins interact in a living cell is a complex problem in biology and in pharmaceutical development.

The ability of an organism to respond to a stimulus is essential for its survival. Disease often results from a breakdown in communication between and within cells. For example, type II diabetes results from the inability of cells to receive and/or process the insulin signal that regulates carbohydrate metabolism. Signals are generally received at the cell membrane by molecules called receptors. The binding of a signaling molecule to a receptor at the outside cell surface causes the receptor to change shape. This, in turn, modulates the chemical activity of the receptor on the inside of the cell. Any given cell will have a number of different receptors enabling it to respond to various signals. The type of tissue from which the cell comes determines which receptors are present on its surface. Different cells respond to different signals, and the same signal can elicit a different response in cells that come from different tissues. For example, epinephrine causes the contraction of vascular smooth muscle but the relaxation of intestinal smooth muscle. How a cell responds to a signal is a result of which proteins are present and activated in the cell at the time of and after the signal is received.

In response to a signal, various proteins in the cell are activated and deactivated. A common strategy used by cells to change the activity of a protein is to add or remove a phosphate group to or from the protein. The addition of a phosphate group to a protein is performed by enzymes (which are themselves proteins) called kinases. Many of the proteins in the above described networks are enzymes. In addition to kinases, many other types of enzymes also exist in cells. Phosphatases, nucleases, glycosidases, lipases and proteases are but a few examples. Enzymes are important drug targets. A challenge in developing drugs against kinases and other types of enzymes is to find molecules that are specific for only the enzyme of interest. Many potential drugs may have a desired effect on its expected target, but may also have an undesired effect on the activity of one or more additional proteins within the cell. Presently available in vitro biochemical assays for enzyme activity often give misleading results since other enzymes and modulators of enzyme activity present in a living cell are not present in the assay (Table I). These factors are difficult to add to an assay because their identity and concentration are often unknown. The situation is further complicated by the fact that the concentration of these factors and the activity of the proteins can change over time (Table II). In order to accurately study the full effect of a drug, all of the components of the signaling pathways must be present and intact.

Thus, it is highly desirable to be able to analyze the activity of a protein in its native cellular environment. Additionally, since the proteins exist in interconnected networks, the activities of many proteins will be affected by perturbations in the cellular environment or by the abnormal activity of another protein within the networks. Thus, it is important to be able to measure the activities of a plurality of proteins at the same time in the cell(s) of interest. We are not aware of any biochemical assay for protein activity capable of measuring the activities of multiple proteins simultaneously in living cells except that described below.

It is now known that many disease states are related to inappropriate protein activity, either too much or too little activity. An example is the human cancer chronic myelogenous leukemia (CML). In most cases of CML a kinase, the protein product of the oncogene bcr-abl, is present in an inappropriately "turned-on" state. This inappropriate activation leads to the uncontrolled growth of blood cells that is manifested as cancer. Other protein products of oncogenes are known to play a role in the development of cancer. However, the presence of the gene or its protein product is not perfectly correlated with the appearance of cancer. A means to measure the activity of such proteins and that of normal proteins in the same cell with the relationships of the protein pathways intact will reveal important insights into disease processes. A profile of a disease composed of a map of the active and inactive proteins in affected cells can be expected to provide a more accurate understanding of the molecular pathogenesis of the disease than even that revealed by current genomic and proteomic techniques (Table III). A database of protein activity in the cells of different tissues, in healthy and diseased cells, and in cells responding to different environmental and pharmacolgic stimuli would have a dramatic impact on biomedical research, pharmaceutical research, and even on our basic understanding of the natural processes of all living organisms.

Existing techniques for the measurement of enzyme activation in a single cell, group of cells, or a portion of a cell have inherent limitations. In recent years much has been made of proteomics, the identification of all proteins produced by an organism, as a means for extending our knowledge beyond the genomics revolution. Unfortunately, current proteomic technologies have significant shortcomings in the study of enzyme function. For the past two decades, the gold standard has been two dimensional-gel electrophoresis. This technique gives a very high resolution for protein separations, but it is difficult to perform, and it cannot detect many important cellular proteins, especially those in low abundance or those with a hydrophobic character (traits typical of many if not most enzymes). The new mass spectrometry techniques combined with bioinformatics have improved the identification of proteins separated by electrophoresis techniques, but do not solve the fundamental issues of performance difficulty and sensitivity. The new chip-based methods hold the as yet unfulfilled promise for identifying large numbers of proteins quickly; however, sensitivity, specificity, and quantification are still issues to resolve. It is important to understand that nearly all current proteomic approaches strive to identify proteins, and in some cases to provide a rough quantitation of protein concentration. However, these approaches do not directly measure the critical parameter of the most crucial proteins: the activity of enzymes. Neither the presence or concentration of an enzyme is a valid measure of its activity. Attempts are made to measure a protein's activity by the identification of a phosphorylated species (many proteins are "switched on" by the addition of one or more phosphate groups), but such an approach can provide only an indirect measure of activity, and detecting such species in a single cell, group of cells, or a portion of a cell is fraught with difficulty.

Until recently, traditional biochemical assays have been the only reliable means of measuring enzyme activity. For kinases most of these methods use the phosphorylation of kinase substrates by cellular extracts or isolated proteins to estimate in vivo kinase activity (FIG. 3). There are three major drawbacks to this approach: 1) the methods have poor sensitivity so that the cytoplasm of large numbers of cells must be pooled; 2) a time-averaged level of the kinase activity is actually measured since the cells are not synchronous with respect to their activation status; and 3) the normal relationships of the pathways and networks within which signal transduction enzymes reside are disrupted. Similar drawbacks exist for measurement of the activity of most other types of enzymes. Recent imaging methods enable some enzymes to be spatially localized in single cells (FIG. 4). Generally the enzyme of interest is labeled within the cell by specific antibodies, inhibitors of the enzyme, or fluorescent tags. Unfortunately, both inactive and active enzyme molecules are highlighted by this method, although some attempt may be made to infer the activity level of the enzyme from its location within the cell. A third strategy still under development is the use of a fluorescent indicator to measure enzyme activity. This strategy has worked well for the measurement of various ion concentrations (i.e., $Ca^{2+}$), but thus far has not been generally applicable to the measurement of enzyme activity in the living cell. A further limitation to all of these techniques is their inability to measure multiple enzyme activities simultaneously in a cell.

BRIEF SUMMARY OF THE INVENTION

The invention is a method of detecting protein activity in a cell, portion of a cell, or group of cells. The method comprises the steps of introducing into the cell reporter molecules which identify one or a plurality of protein activities. The reporter molecules are released from the cell, and exposed to a sensor which senses reporter molecules of one or a plurality of protein activities.

The invention can also be defined as a method of producing a description of the protein activity of a cell, portion of a cell, or cells comprising the steps of introducing into the cell reporter molecules which respond to protein activity in the cell; releasing the reporter molecules from the cell; sensing the released reporter molecules; recording the protein activity indicated by the reporter molecules; and compiling a tabulation of protein activity corresponding to the state of protein activity within the cell or cells.

The invention is further defined as a method of producing a description of the protein activity of a cell, portion of a cell, or cells in response to an external stimulus or stimuli comprising the steps of introducing into the cell reporter molecules which respond to protein activity in the cell; exposing the cell to an external stimulus or stimuli; releasing the reporter molecules from the cell; sensing the released reporter molecules; recording the protein activity indicated by the reporter molecules; and compiling a tabulation of protein activity corresponding to the external stimulus or stimuli.

In one embodiment the external stimulus is a pharmaceutical compound. The tabulation is a compilation of cellular protein activity responsive to the pharmaceutical compound. The tabulation is a map of cellular response to the pharmaceutical compound. The cellular response comprises at least one of desired cellular response and undesired other response.

The reporter molecules are introduced into the cell by attachment to an auxiliary molecule or polymer which is taken up into a cell or cells. The auxiliary molecule is a peptide or peptide analog.

The reporter molecules are labeled to facilitate detection. The label consists of a fluorescent group, stable or radioactive isotope, or biotin. The reporter molecules may have the same or different labels. Additionally, the fluorescent groups used to label the reporters may have different spectral properties such that reporter molecules so labeled can be detected, separated, and identified based on their spectral properties irrespective of their electrophoretic properties.

In one embodiment the reporter is present at a subphysiologic concentration compared with the concentration of the native substrate. The concentration of any one reporter is less than or equal to 10 micromolar, preferably less than or equal to 1 micromolar, or less than or equal to 100 nanomolar.

In another embodiment a chemical reaction involving the reporter is diminished or terminated by liberating the reporter and altered reporter from the cell or cells. In still another embodiment the chemical reaction involving the reporter is diminished or terminated by dilution. In yet another embodiment chemical reaction involving the reporter is stopped by the use of scavengers or inhibitors. In a further embodiment the reporter is labeled and a chemical reaction involving the reporter is stopped by the introduction of unlabeled reporter. In one embodiment the chemical reaction involving the reporter is stopped before liberating the reporter and the unaltered reporter from the cell or cells. In an embodiment the scavenger, inhibitor, or unlabeled reporter is introduced photochemically from a caged scavenger, inhibitor, or unlabeled reporter. In another embodiment the chemical reaction involving the reporter is stopped after liberating the reporter and/or unaltered reporter from the cell and or cells.

In one of the illustrated embodiments the time between liberating the reporter and/or altered reporter from the cell or cells and stopping a chemical reaction involving the reporter is variously less than 1 second, less than 33 milliseconds or even less than 10 microseconds.

In various embodiments the reporter and altered reporter are distinguished by electrophoresis, microchromatography, mass spectroscopy, fluorescence spectroscopy, fluorescence polarization spectroscopy, affinity array, or other means. Distinguishing reporter molecules by labeling the molecules with tags possessing various spectral properties and separating them by virtue of their unique spectral characteristics by fluorescence spectroscopy is specifically contemplated.

In various embodiments the reporter and/or altered reporter are sensed by fluorescence spectroscopy, polarization techniques, mass spectroscopy, conductivity, radioactive detection, or other means.

The methods described above can be used for any purpose in combination with two dimensional gel electrophoresis, protein mass spectroscopy, yeast 2-hybrid assays, structural biology, intracellular ion and other indicators, intracellular protein location techniques, DNA arrays, and flow cytometry (including sheathed and unsheathed flow and flow cytometry on a microfluidics device). The protein activity of three or more proteins is detected and/or quantified and preferably the protein activity of four, five, six, ten or more proteins is detected and/or quantified. Specifically, the protein activity of three, four, five, six, ten or more proteins in a cell, portion of a cell, or group of cells is detected and/or quantified. The invention contemplates the detection and/or the quantification of the protein activity of three, four, five, six, ten or more proteins in a cell, portion of a cell, or group of cells.

Thus, the invention be characterized as a method for assessing protein activity in a cell by introducing three or more reporters of protein activity in a cell or group of cells.

It can also be characterized as an apparatus for measuring the protein activity in a cell or cells of one or a plurality of proteins comprising a means of lysing the cell or cells, a means for collecting the contents or a portion of the contents of a cell or cells, a means for distinguishing reporter molecules and altered reporter molecules; and a means for sensing reporter molecules and/or altered reporter molecules.

Alternatively, the invention is an apparatus for measuring the protein activity of one or a plurality of proteins comprising a means of lysing the cell or cells, a means for collecting the contents or a portion of the contents of the cell or cells, a means for distinguishing reporter molecules and altered reporter molecules, a means for sensing reporter molecules and/or altered reporter molecules, a means of recording the protein activity indicated by the reporter molecules; and a means of compiling a tabulation of protein activity.

The apparatus further comprises a means to introduce reporter molecules into the cell or cells. The means of introduction of reporter molecules includes microinjection, optoinjection, optoporation, electroporation, or by attachment of an auxiliary molecule causing the reporter to pass into the cell or cells. The apparatus further comprises a means to present cells to the collection device. The means of cell presentation is a multi-well plate, a dielectrophoresis trap, laser tweezers, a microlumen or array of microlumens, or other means. The means of collection is aspiration through a microlumen. The means of collection is a microlumen, microwell, nanowell, picowell, or microfluidics chip. The means of lysing the cell is a laser, a shock wave, piezo-electric-mediated ultrasound wave, application of an electric field (AC or DC) or treatment with a chemical reagent. The means of distinguishing is electrophoresis, microchromatography, mass spectroscopy, affinity arrays, or other means. The affinity array is an array of biomolecules such as DNA, RNA, PNA, proteins, receptors, enzymes, or antibodies. The means of distinguishing is electrophoresis conducted on a microfluidics device. The means of sensing is fluorescence spectroscopy, mass spectroscopy, conductivity, or radioactive detection.

The apparatus further comprises a computer controlled collection device, a computer-controlled lysis device, a computer-controlled distinguishing device, a computer-controlled sensing device, a data processor coupled to the sensor to record changes in the reporter, and/or data processor to compile a tabulation of protein activities.

The invention is a method for assessing protein activity in a cell by introducing three, four, five, six, ten or more reporters of protein activity in a cell or group of cells. The invention is a method for elucidating cellular signaling pathways using electrophoresis in a capillary or a microlumen. It is a method for elucidating cellular signaling pathways comprising analysis of a plurality of enzymatic reactions using electrophoresis in a capillary or a microlumen. It is a method for elucidating cellular signaling pathways comprising the steps of introducing reporters of enzymatic reactions into a cell or cells; collecting the reporters; and analyzing the reporters using electrophoresis in a capillary or a microlumen.

While for the purposes of grammatical fluency the invention has in some instances been described as a step or means for performing a function, it is to be expressly understood that the invention is directed to acts and to structure without necessarily being defined or limited by any related function performed by the act or structure. Hence, the invention is not to be construed from the above description as limited by the construction of means and steps under 35 USC 112. The invention can be better visualized by turning to the following drawings wherein like elements are referenced by like numerals.

BRIEF DESCRIPTION OF THE DRAWINGS

FIGS. 6A(1)–(3) are schematics of examples as to how a microlumen could be positioned near a portion of a cell so that only a small portion of the cell is analyzed.

Figure 1:
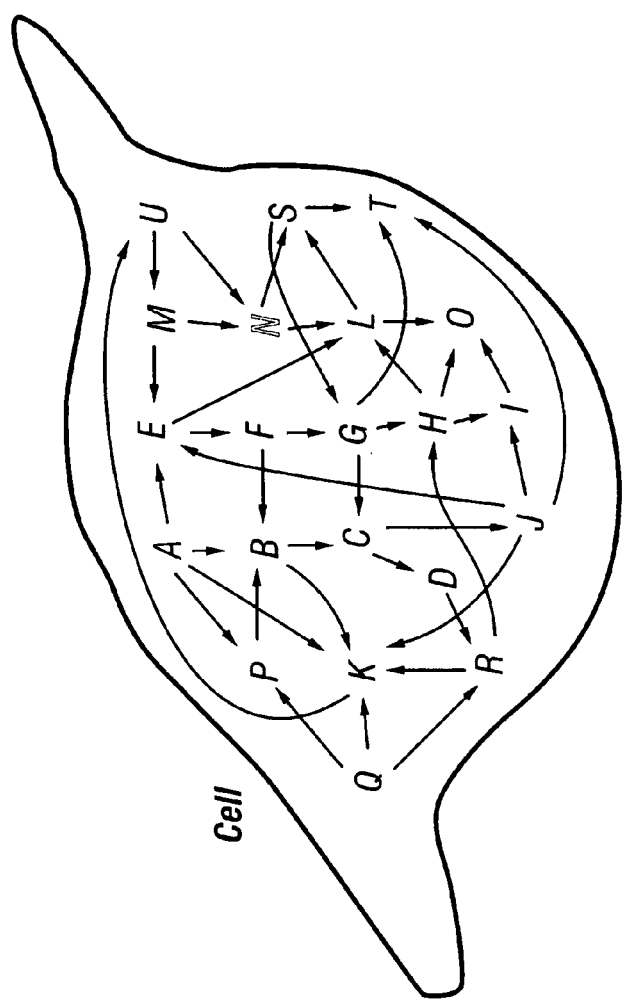
FIG. 1 is a diagram of a cell depicting a complex, interacting network of proteins. Each letter represents a protein and the arrows represent how the proteins might interact with one another.

The illustrated embodiment of the invention and its definition as set forth in the claims may now be better understood by turning to the following description of the preferred embodiments of the invention.

DETAILED DESCRIPTION OF THE PREFERRED EMBODIMENTS OF THE INVENTION

The activity of multiple proteins in a single living cell, portion of a cell or in a group of cells are simultaneously examined. A database is compiled from the application of this method to cells under a large variety of different conditions. The protein activity is measured by introducing one or more reporter molecules (substrates) into one or more cells. The reporter(s) is chemically modified by the enzyme of interest. In some cases the enzyme(s) of interest is affected by the addition of a stimulus or a pharmaceutical compound to the cell. The reactions between the enzymes and the reporters are diminished or terminated, and the reporter and modified reporter are removed from the cell. The activity of the enzyme(s) is determined by measuring the amount of reporter molecules remaining, by measuring the amount of altered reporter molecules produced, or by comparing the amount of reporter molecules to the amount of altered reporter molecules. A database is compiled of the activities of the different proteins. By performing a series of experiments at different time points, under varying conditions, and with a variety of cell types, the database is developed into a valuable repository of knowledge for understanding the molecular mechanisms of cell behavior in health and disease states. By exposing cells to a variety of compounds the method provides valuable data for drug development and screening.

The invention is an apparatus and method to simultaneously examine the activity of multiple proteins in a single living cell 14, portion of a cell 14 or in a group of cells 14 (FIGS. 5–6). FIG. 5A is a schematic of the microlumen's placement over either a single cell 14 or a group of cells 14 to be analyzed according to the invention. In the upper portion of FIG. 5A microlumen 10 having an aperture 12 is disposed in proximity to a plurality of cells 14. The diameter of aperture 12 is just sufficient to allow the uptake of a single cell 14. In the lower portion of FIG. 5B microlumen 10' has an aperture 16 which is disposed in proximity to a plurality of cells 14. The diameter of aperture 16 is sufficient to allow the uptake of multiple cells 14 at or about the same time, or at least in or during the time period of analysis relating to their collective uptake into microlumen 10'.

Figures 1, 5A:
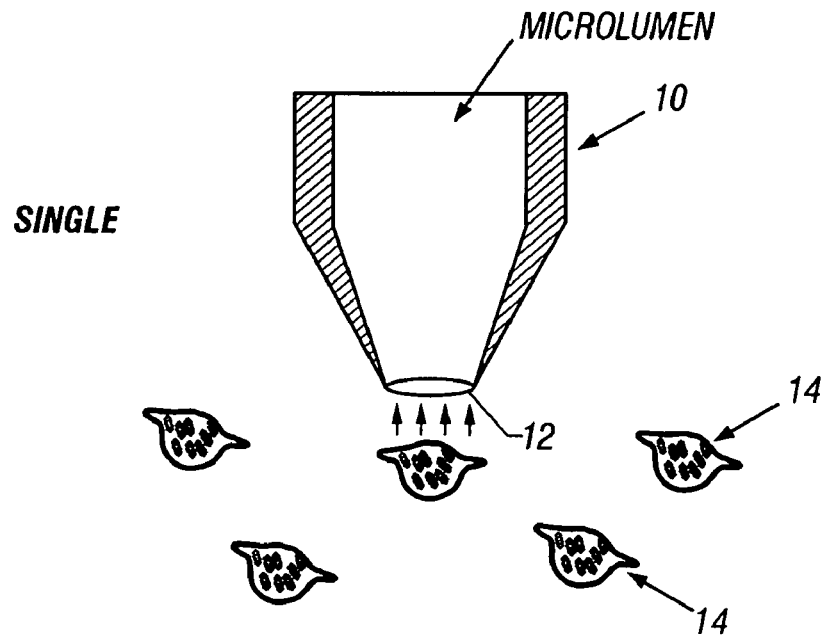
FIG. 5A is a schematic of the microlumen's placement over either a single cell or a group of cells to be analyzed according to the invention.
Figures 2, 5A:
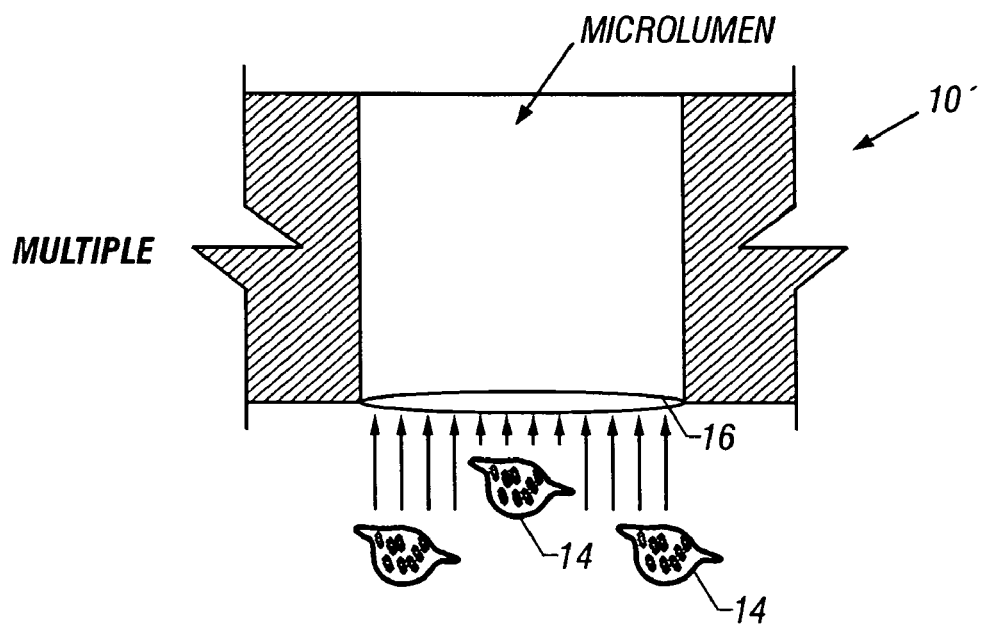
Figure 5B:
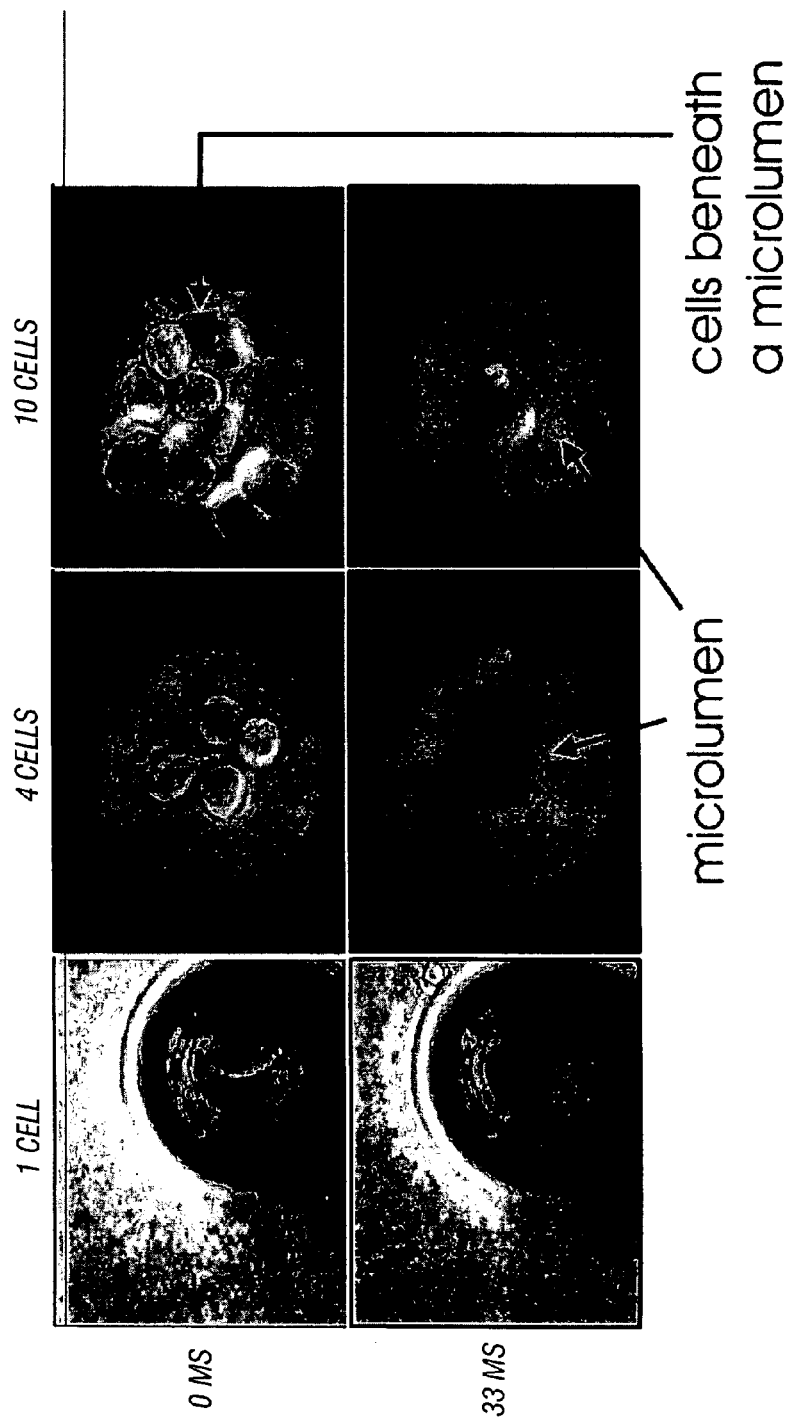
FIG. 5B is a collection of microphotographic images before (0 ms) and after (33 ms) simultaneous sampling of either 1, 4, or 10 cells taking by the devices diagrammatically depicted in FIG. 5A.

FIG. 5B is a collection of microphotographic images before (0 ms) and after (33 ms) simultaneous sampling of either 1, 4, or 10 cells 14. The microphotographic images are arranged in two rows of three columns with the top row being before sampling and the bottom row after sampling.

Figure 5C:
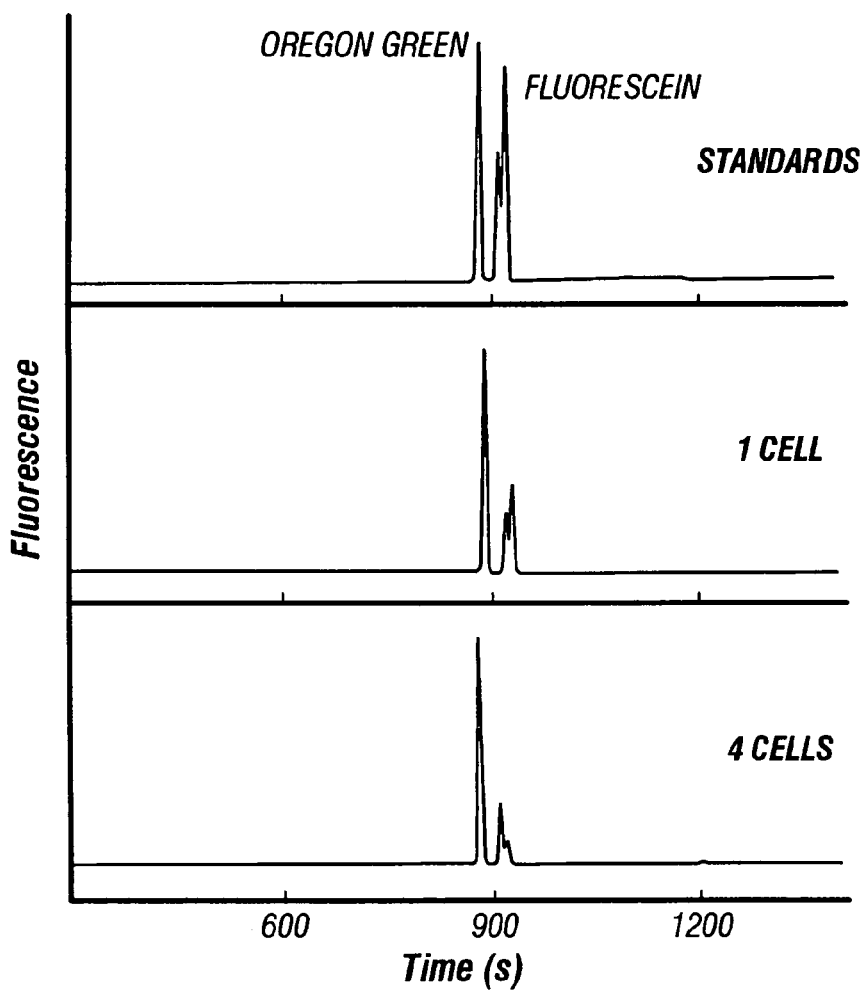
FIG. 5C shows typical electropherograms in which a standard and the contents of 1 or 4 cells were analyzed such as are depicted as being sampled in FIG. 5B. The cells were previously loaded with Oregon Green and two isomers of fluorescein.

The first column shows a single cell 14, the middle column shows four cells 14, and the rightmost column shows ten cells 14. The microphotographic images clearly show uptake of single, four and ten cells 14. It is to be understood that by use with conventional cellular manipulation instruments the number of cells 14 which can be simultaneously sampled or sampled as a group is arbitrary and is limited only by the orifice of the microlumen used for uptake and the uptake volume. FIG. 5C shows typical electropherograms in which a standard and the contents of 1 or 4 cells 14 were analyzed. Cells 14 were previously loaded with Oregon Green and two isomers of fluorescein.

Figure 2:
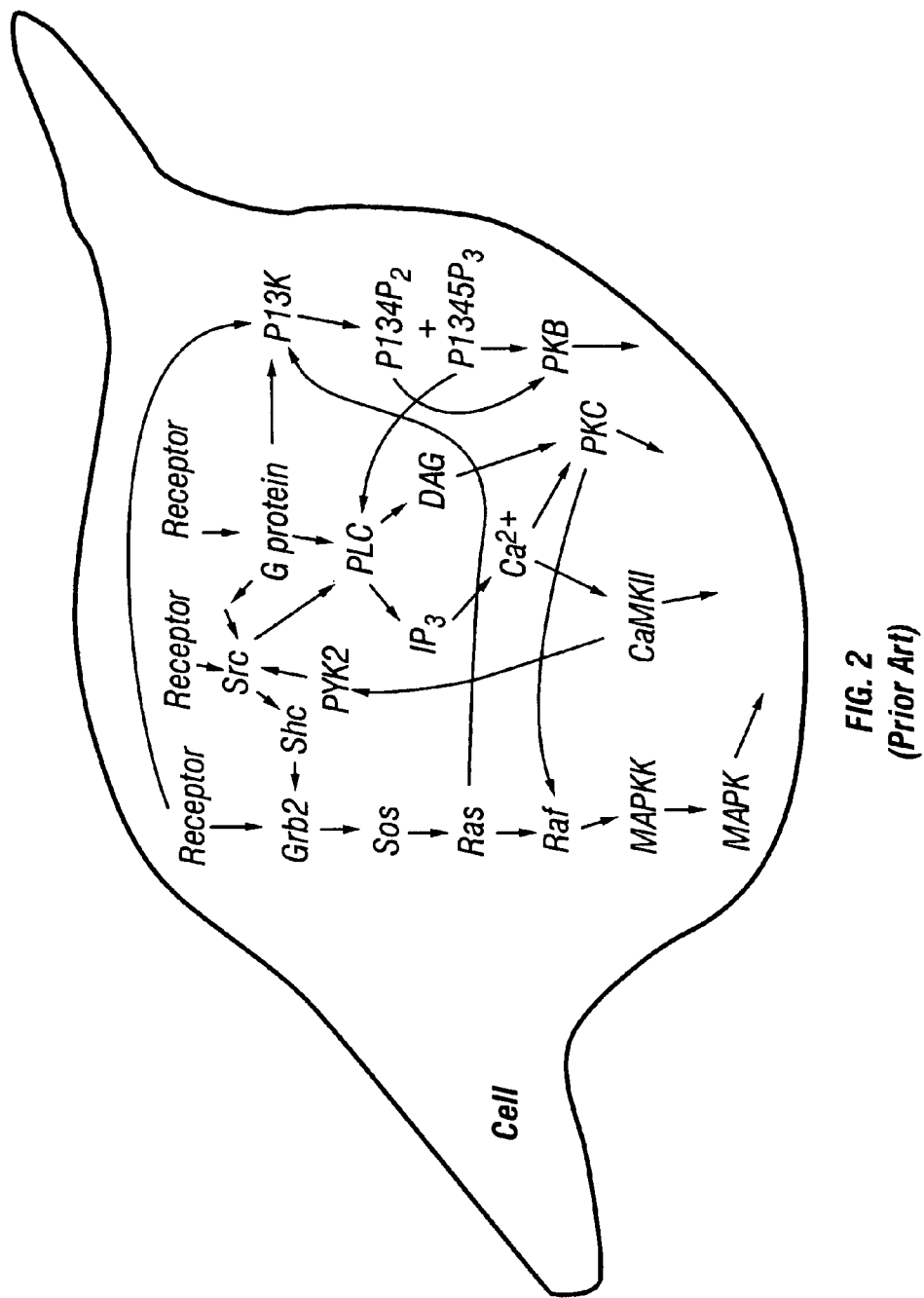
FIG. 2 is a diagram of three known protein pathways: the mitogen activated protein (MAP) kinase cascade, the phosphoinositide cascade, and the phosphatidyl inositol-3 kinase cascade. Many of the known elements in the pathways are shown as abbreviations (i.e. Sos, ras, etc.) and the arrows represent which of the molecules might interact with other members of the pathways. Most of the elements or molecules in these cascades are enzymes (as are the elements in other enzyme cascades or signaling networks).
Figure 3:
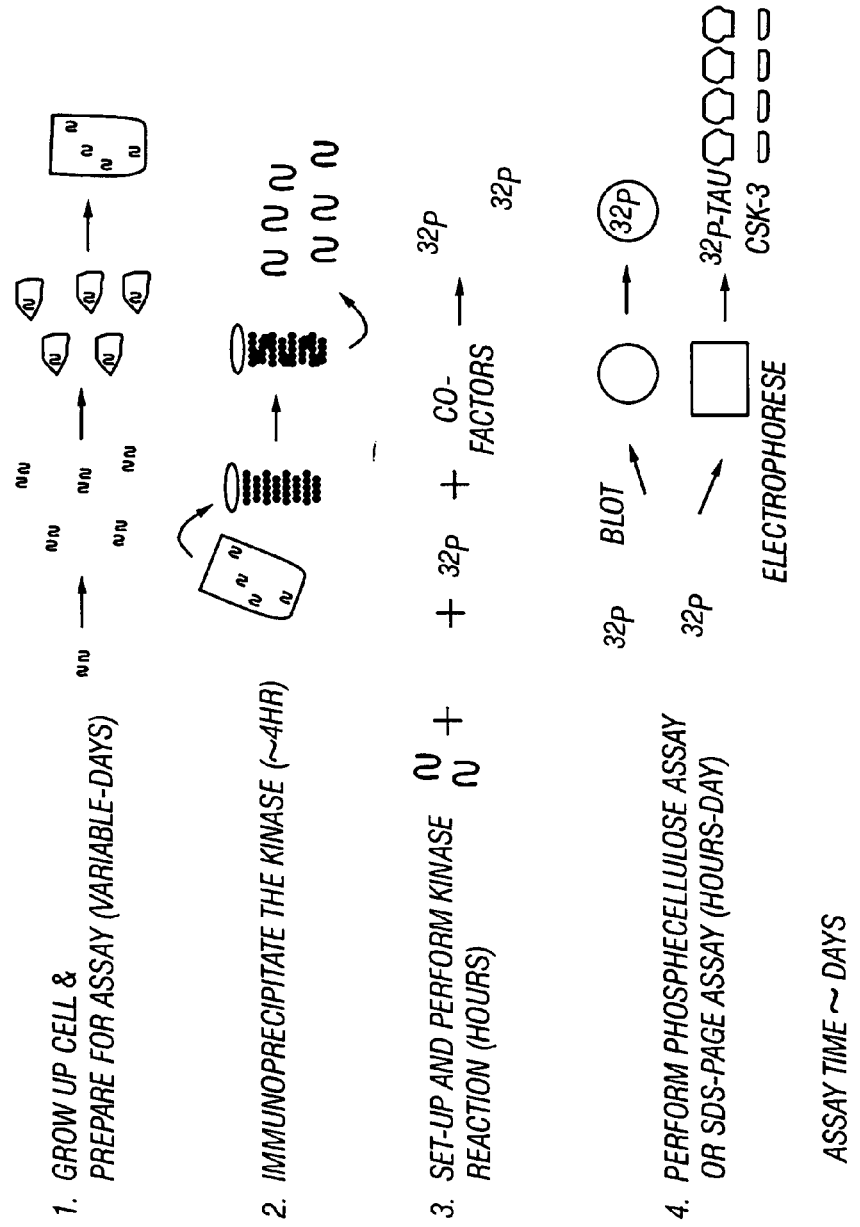
FIGS. 3 and 4 display examples of the current assays for performing measurements of enzyme activity. The technology shown in FIG. 3 lacks the sensitivity for single cell measurements. Additionally it requires many steps, is extraordinarily time consuming and requires a large amount of manpower. The technology shown in FIG. 4 is an indirect measure of enzyme activation and so is prone to artifact. Additionally it is limited to only a small subset of enzymes, those that translocate within the cell. No assay format can perform measurements of multiple enzymes simultaneously.
Figure 4:
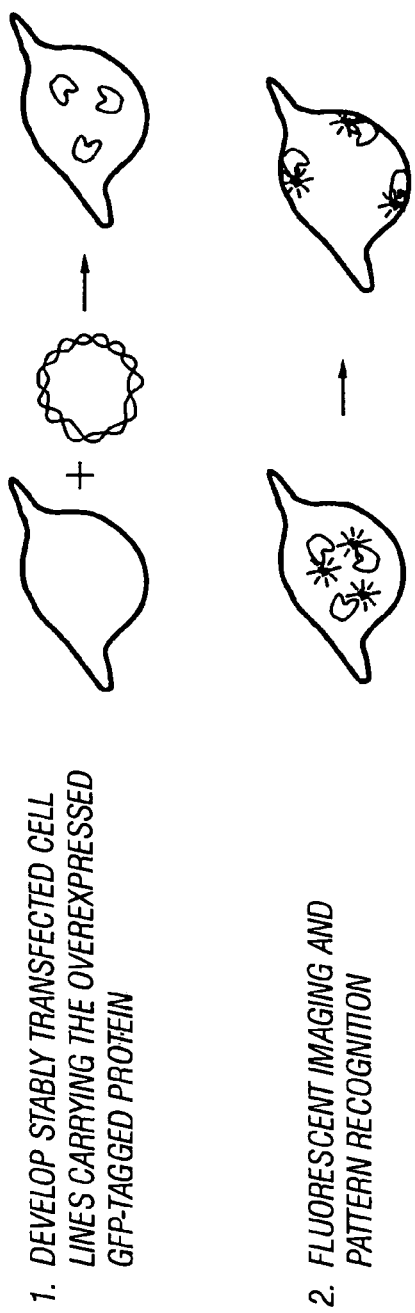
Figure 6B:
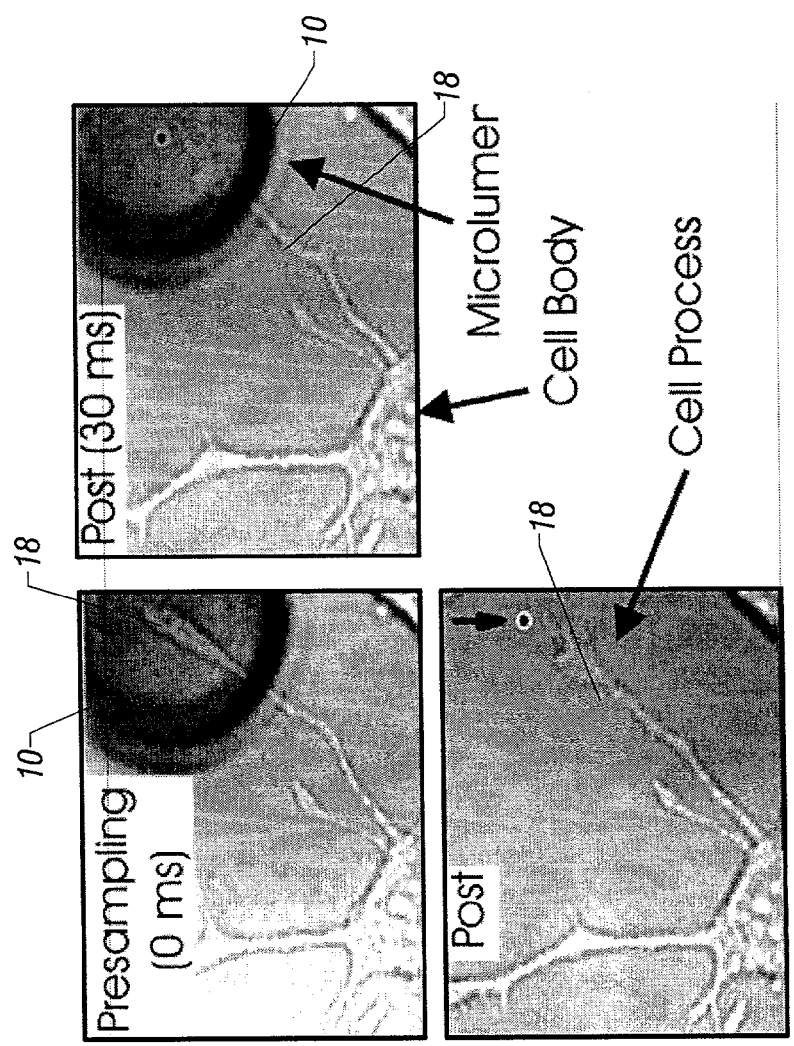
FIG. 6B is a collection of microphotographic images of a cell before and after sampling of one of the cell's processes as diagrammatically depicted in FIG. 6A.
Figure 6C:
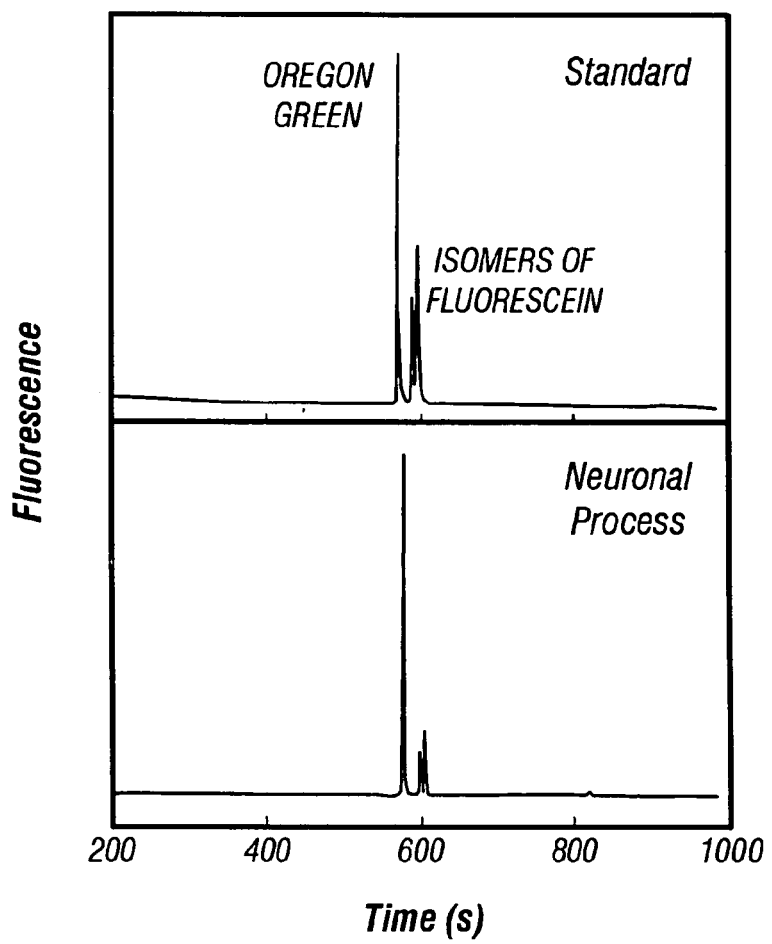
FIG. 6C shows typical electropherograms of standards of Oregon Green and two isomers of fluorescein or of the contents of a process of a cell which had been previously loaded with Oregon Green and the two isomers of fluorescein as shown in FIG. 6B.

Not only arbitrary numbers of cells 14 can be sampled, but portions of cells 14 in many cases can be sampled. FIG. 6A–1 is a diagrammatic depiction where microlumen 10 is positioned and used to sample the distal end of an extended process 18 of cell 14. FIG. 6A–2 is a diagrammatic depiction where microlumen 10 is positioned and used to sample a more proximal portion of process 18 of cell 14. FIG. 6A–3 is a diagrammatic depiction where a microlumen 20 is positioned next to or defined as part of a microfluidics chip 22 and is used to sample a process 24 of cell 14 disposed in microlumen 20. FIG. 6A–3 also provides a diagrammatic depiction where a microlumen 20 is positioned next to or defined as part of a microfluidics chip 22 and is used to sample a distal end 26 of a process of cell 14 disposed in or near an inlet to microlumen 20. The diagrammatic depiction of FIGS. 6A–1 to 6A–3 are shown in the case of an actual cell 14 in the photomicrographs of FIG. 6B where a presampled image, an image of cell 14 and its process at 30 ms after imaging and then an image after microlumen 10 is removed in which the center of the position of the orifice of microlumen 10 relative to cell 14 is denoted by a black dot. The distal end of the process 18 can be clearly seen as being removed by comparing the presampling and post sampling images. FIG. 6C depicts two electropherograms, one shows a standard of Oregon Green and two isomers of fluorescein, and the other shows the analyzed contents of process 18 of cell 14, which had been previously loaded with Oregon Green and the same two isomers of fluorescein.

A database from applications of this invention to cells 14 under a large variety of different conditions is compiled. A device with the capability to assay the activity of multiple proteins in living cells 14 is achieved through the preferred embodiments by use of an apparatus described in application Ser. No. 09/036,706 filed Mar. 6, 1998, and entitled "Fast Controllable Laser Lysis of Cells for Analysis", and the continuation-in-part application Ser. No. 09/358,504 filed Jul. 21, 1999 and entitled "Method and Apparatus for Detecting Enzymatic Activity Using Molecules that Change Electrophoretic Mobility", to which this application is related and both of which applications are herein expressly incorporated by reference.

Figure 7A:
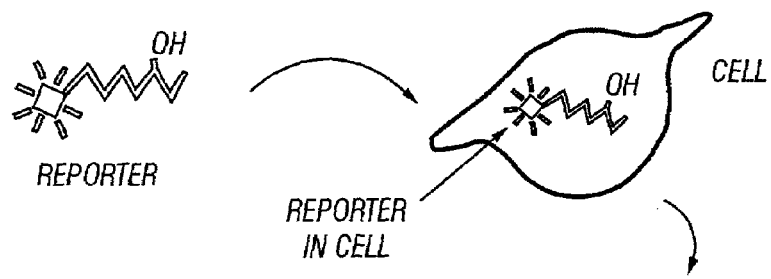
FIGS. 7A–C are schematic illustrations of the assay used to measure enzyme activity in a cell, a group of cells, or a portion of a cell. As an example, a kinase assay is depicted.
Figure 7B:
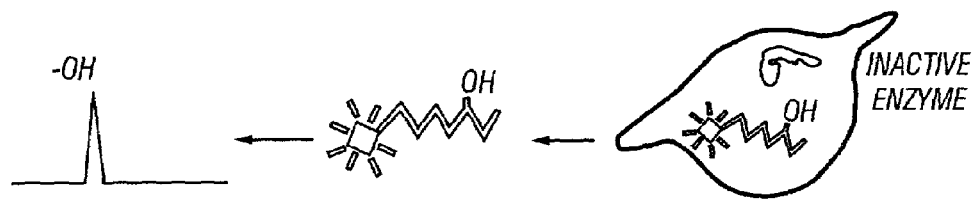
Figure 7C:
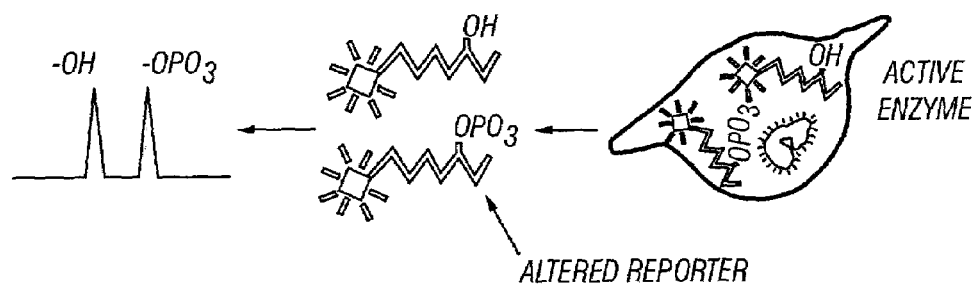

In the invention, protein activity is measured by introducing one or more reporter molecules (substrates) into one or more cells 14. The reporter(s) is chemically modified by the enzyme of interest. In some cases the enzyme(s) of interest is affected by the addition of a stimulus or a pharmaceutical compound to the cell 14. The reactions between the enzymes and the reporters are diminished or terminated, and the reporter and modified reporter are removed from the cell 14. The activity of the enzyme(s) is determined by measuring the amount of reporter molecules remaining, by measuring the amount of altered reporter molecules produced, or by comparing the amount of reporter molecules to the amount of altered reporter molecules. FIG. 7A diagrammatically illustrates the introduction of a reporter molecule 28 into cell 14. An inactive enzyme 30 in cell 14 has no chemical reaction with reporter 28, which is then extracted from cell 14 and is measured as an unaltered reporter 28 by electropherogram 32. In FIG. 7C an active enzyme 30' reacts with at least some of reporters 28 to form some altered reporters 28', both of which reporters 28 and 28' are extracted and then both detected and measured in electropherogram 32'.

The database is compiled of the activities of the different proteins. By performing a series of experiments at different time points, under varying conditions, and with a variety of cell types, the database is developed into a valuable repository of knowledge for understanding the molecular mechanisms of cell behavior in healthy and diseased states. The application of this method while exposing cells 14 to a variety of compounds provides valuable data for drug development and screening.

Figure 8A:
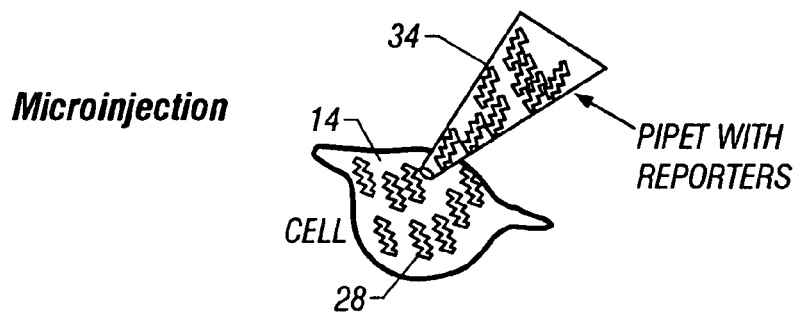
FIG. 8 is a collection of schematics of several examples showing how a single cell can be loaded with reporter molecules.
Figure 8B:
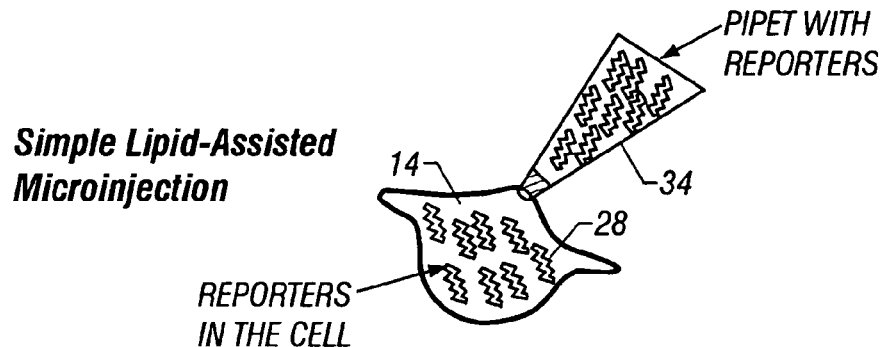
Figure 8C:
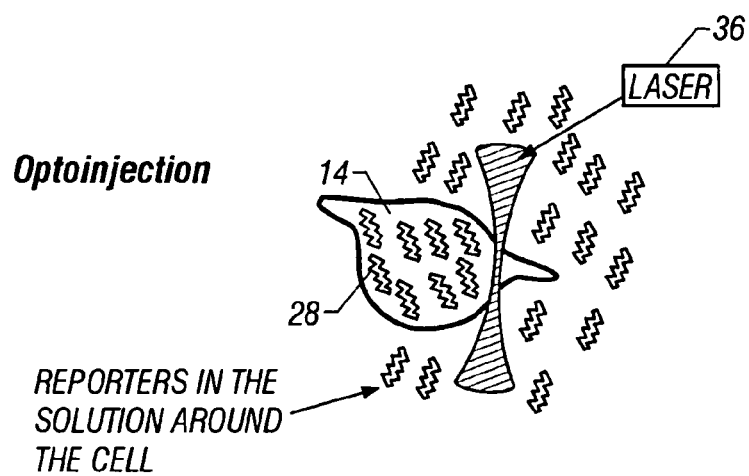
Figure 9A:
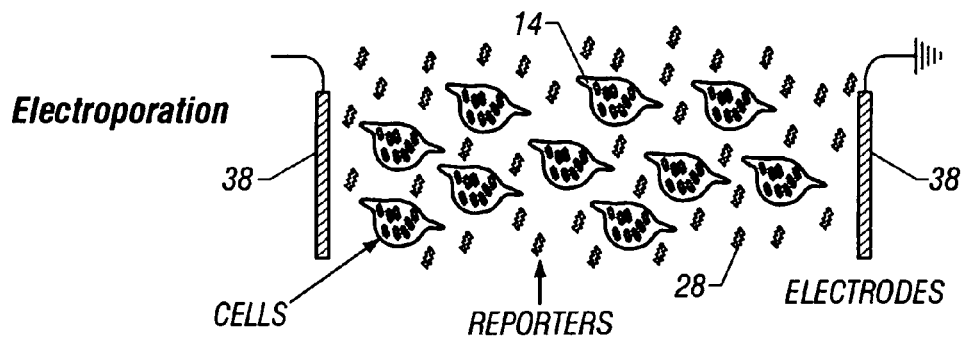
FIG. 9 is a collection of schematics of several examples as to how multiple cells can be loaded with reporter molecules.
Figure 9B:
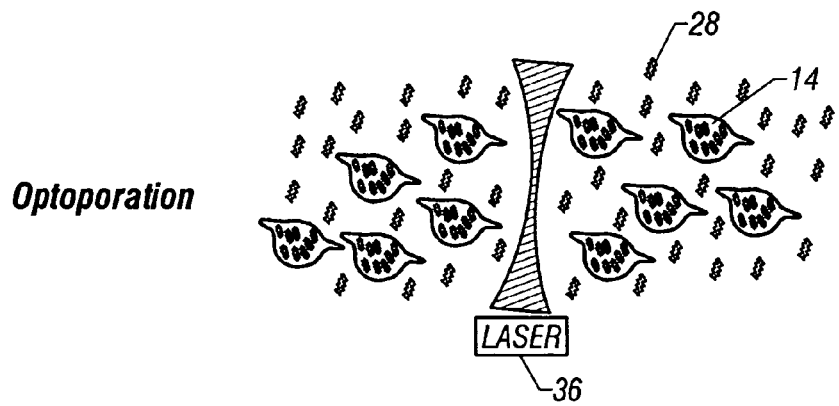
Figure 9C:
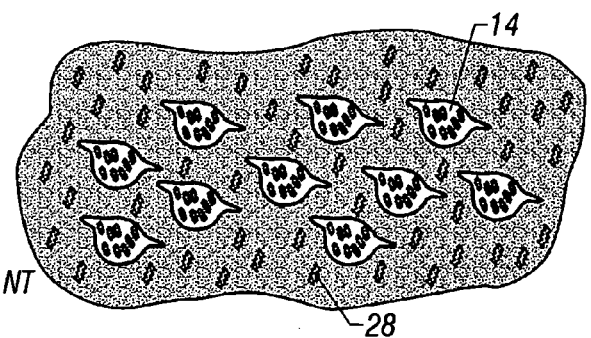
Figures 10A, 10B:
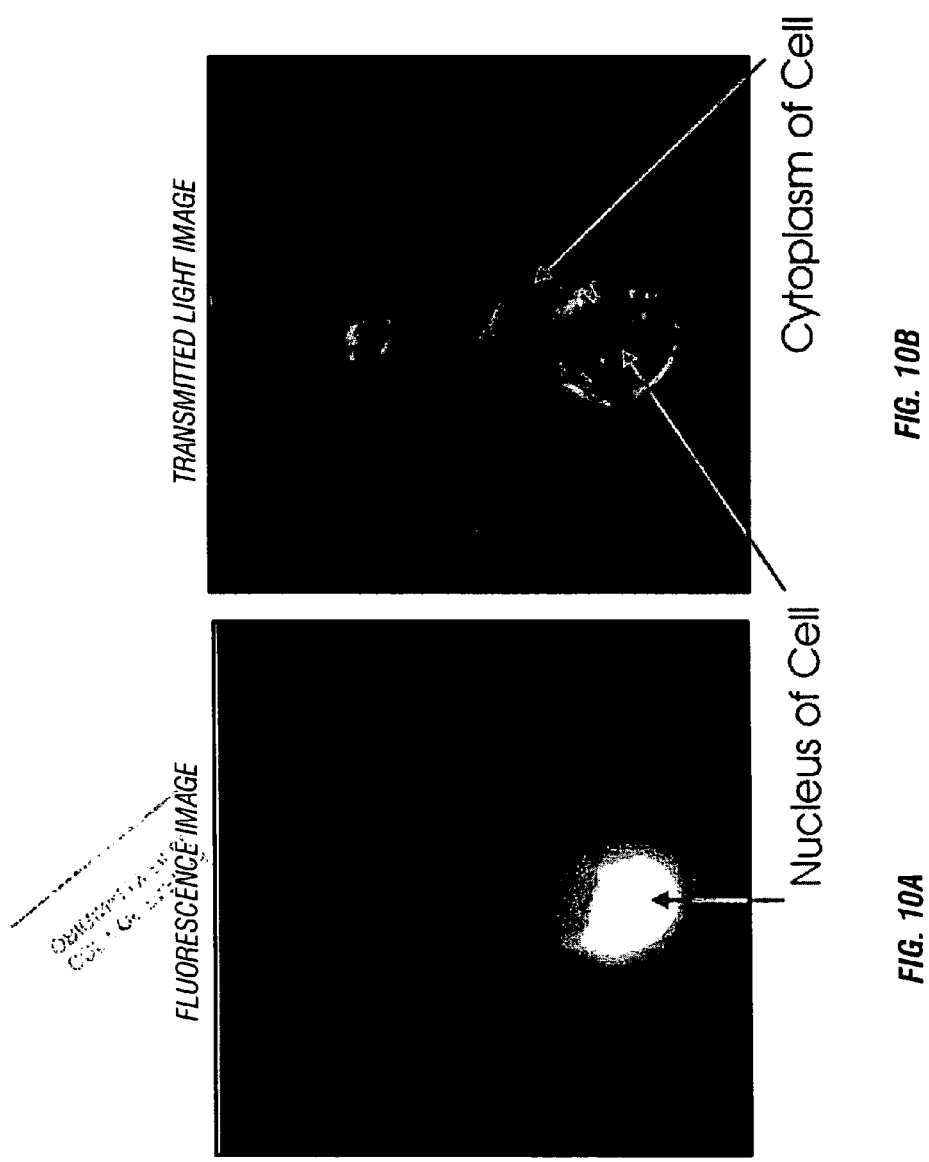
FIG. 10 shows fluorescent and transmitted light images of a cell loaded with reporter molecules for protein kinase C (PKC) localized to the nucleus.

There are many methods by which the reporter can be introduced into the cell 14. These include but are not limited to microinjection, optoporation, optoinjection, electroporation, vesicle fusion and pinocytosis. FIG. 8 diagrammatically illustrates how a single cell 14 can be loaded with reporter molecules 28 with a pipette 34 by microinjection of simple lipid-assisted microinjection, or by optoinjection using a laser 36. FIG. 9 diagrammatically illustrates how multiple cells 14 can be loaded with reporter molecules 28 by electroporation in a solution between electrodes 38, by optoporation in a solution carrying reporters 28 by using laser 36, and by any one of various passive techniques such as by use of pinocytosis, vesicle formation, and membrane-permeant substrates. The reporter 28 can also be introduced into the cell 14 by covalently attaching it to an auxiliary molecule that is transported into the cell 14. These auxiliary molecules include, but are not limited to, the HIV-TAT peptide, antennapedia peptide, VP22 peptide, and their analogs. It can also be a peptide sequence that targets the reporter 28 to localization into specific subcellular organelles, which is photographically illustrated in FIG. 10 in which a nuclear-localized substrate for PKC is shown in a fluorescent image in the left and in a transmitted light image in the right of a cell 14 loaded with reporter molecules 28 for protein kinase C (PKC) localized to the nucleus. The reporter for PKC was fused with an auxiliary molecule, a peptide known as a nuclear localization sequence (NLS). The combination of the two molecules causes the resulting molecule (NLS-PKC) to be selectively localized in the cell's nucleus.

The attachment of the reporter 28 to the auxiliary molecule can be direct, or it can be through a linker molecule. The linker molecule can be non-cleavable or it can be intracellularly cleaved so that the reporter 28 and the auxiliary molecules are no longer attached once in the cell 14. The reporter 28 can be unlabelled or have an attached label to facilitate the reporter's detection. A few examples of labels include, but are not limited to, fluorophores, stable isotopes, radioactive isotopes, and biotin. Labels that are similar but differ in some minor way that allows them to be distinguished (e.g. fluorophores with different spectral properties) can be used. In addition cells 14 can be caused to produce a reporter molecule 28 through standard techniques from molecular biology. The variety of biomolecules produced by fusing green fluorescent protein or its derivatives with the molecule of interest is such an example.

To minimize any effects the reporter 28 might have on the system being studied, the concentration of the reporter 28 in the cell 14 is ideally less than or similar to the concentration of the normal substrate for the enzymes 30 whose activity is being determined. The technique can be used to detect enzyme activity when the concentration of the reporter 28 in the cell 14 is as low as 100 nanomolar. Single molecules can now be detected so cellular concentrations of reporters 28 as low as 10 nM can be utilized.

The reaction between the reporter 28 and the enzyme 30 being studied can be diminished or stopped by dilution of the cellular contents, or by adding scavengers, enzyme inhibitors, or unlabeled reporter 28. The reaction can be terminated coincident with the reporter 28 being removed from the cell 14, prior to the reporter 28 being removed from the cell 14 or after the reporter 28 is removed from the cell 14. If the reaction is stopped after the liberation of the reporter 28 from the cell 14, it is ideal that the time between liberating the reporter 28 from the cell 14 and stopping the reaction is less than 1 second. For some cell types, such as neuronal cells 14, certain enzymatic reactions must be stopped in less than 33 ms. Given the reaction rates of enzymatically catalyzed reactions of biomolecules, in all cases terminating the reactions in less than or equal to 10 microseconds is well beyond the temporal resolution needed for accurate measurements.

The extent to which the reporter 28 has been modified by the enzyme 30 of interest can be determined by distinguishing the reporter 28 and modified reporter 28' and then quantifying either or both the reporter 28 and the modified reporter 28'. Methods of distinguishing the reporter 28 and the modified reporter 28' include but are not limited to separation by electrophoresis, microchromatography, mass spectroscopy and affinity arrays of DNA, proteins, and other molecules. Methods of quantifying the amount of reporter 28 and/or altered reporter 28' include, but are not limited to, fluorescence spectroscopy, fluorescence polarization spectroscopy, mass spectroscopy, electrochemical detection, conductivity, radioactive detection or ELISA techniques.

Figure 11:
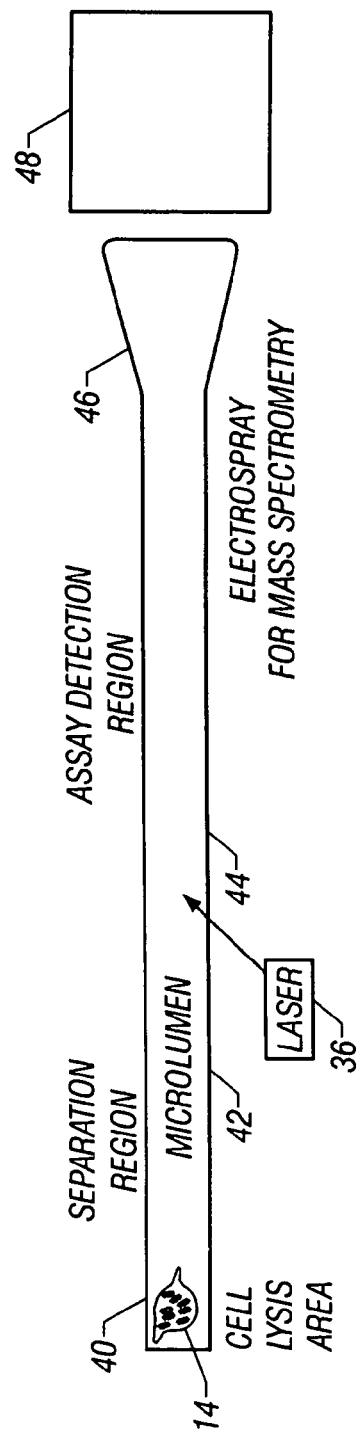
FIG. 11 depicts an example as to how the assay might be combined with mass spectroscopy.
Figure 12A:
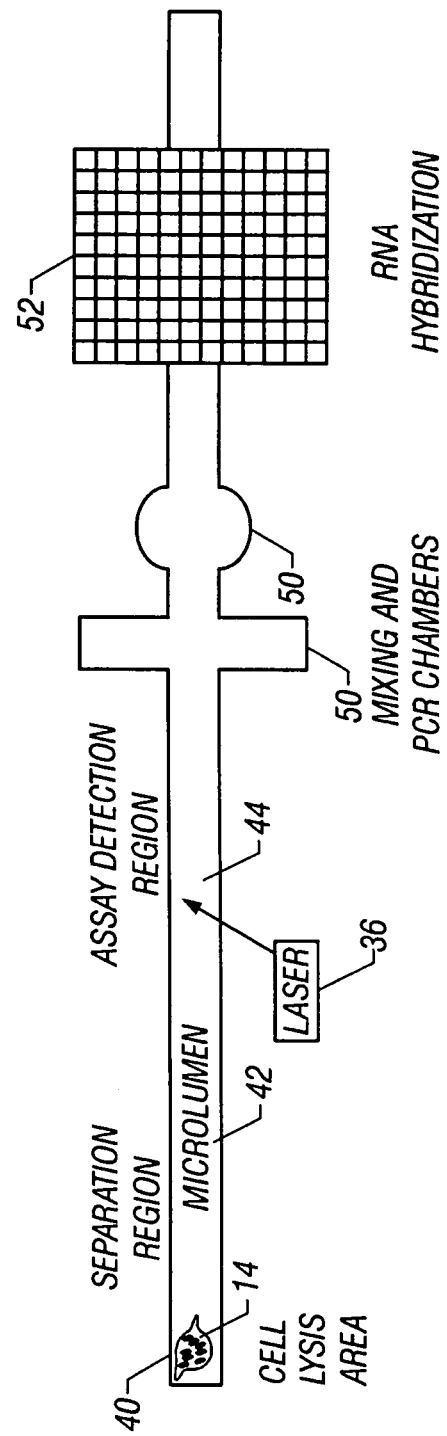
FIGS. 12A and B show examples as to how the assay might be combined with DNA arrays.
Figure 12B:
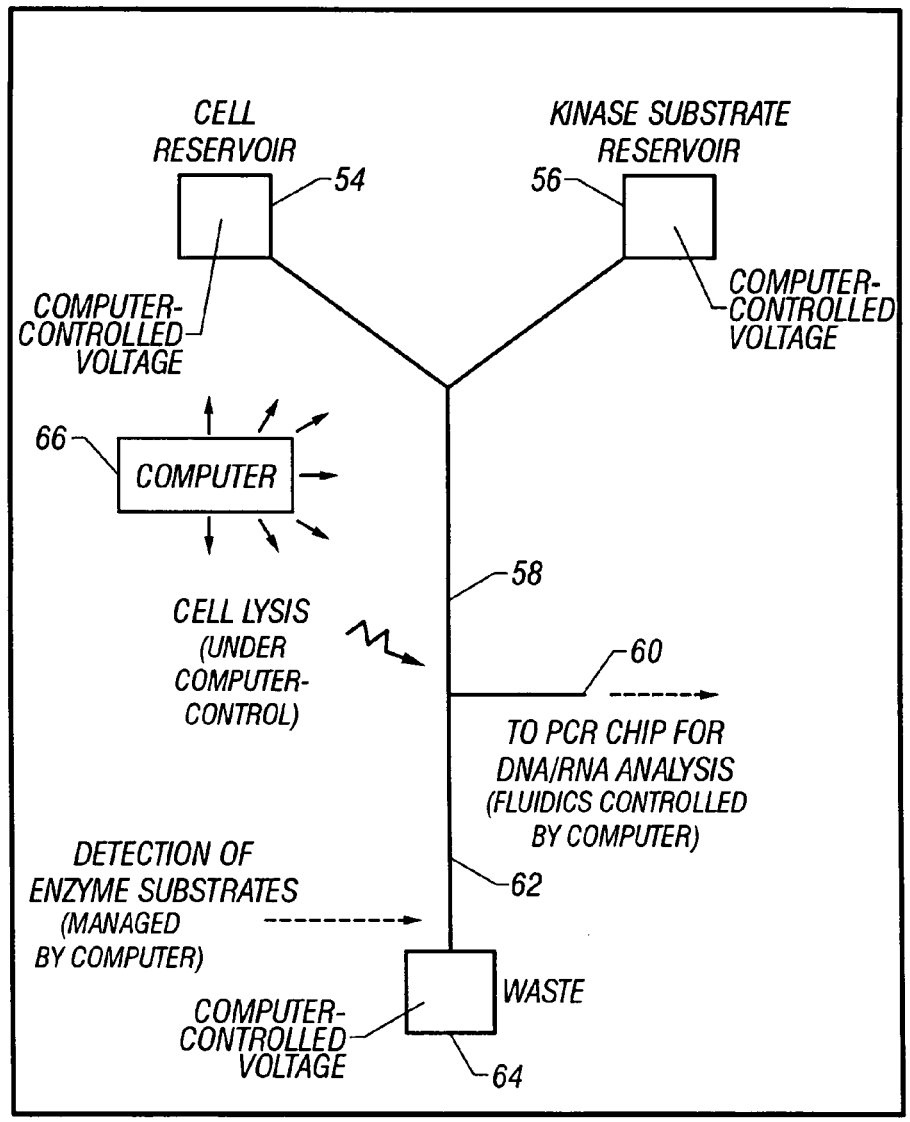

To assess more completely the activity of cells 14 or populations of cells 14, the described technique for measuring protein activity can be used in combination with other techniques commonly used in molecular and cellular biology. Such techniques include, but are not limited to, flow cytometry, flow cytometry conducted on a microfluidics device, two dimensional gel electrophoresis, protein mass spectroscopy, structural biology, intracellular ion and other indicators, intracellular protein location techniques (including, but not limited to, antibody and green-fluorescent-protein based methods), and affinity arrays. FIG. 11 diagrammatically illustrates proteomic assay using a mass spectrometer 48 in which cell 14 is lysed in area 40, electrophoretically separated in microlumen 42, fluorescently detected by laser 36 in assay detection region 44, and dispersed in an electrospray 46 for analysis in mass spectrometer 48. FIG. 12A illustrates a genomic assay in which cell 14 is lysed in area 40, electrophoretically separated in microlumen 42, fluorescently detected by laser 36 in assay detection region 44, and mixed and replicated in mixing and PCR chambers 50 to be assayed using RNA hybridization array 52. FIG. 12B diagrammatic depicts a signal transduction microchip in which cells 14 from reservoir 54 are mixed with kinase substrates from reservoir 56 as controlled by computer 66 to be lysed at area 58. The cell contents are either directed to a PCR chip 60 for DNA/RNA array analysis using computer controlled microfluidics or are fluorescently detected at 62 and thereafter deposited in a waste reservoir 64.

Figure 13:
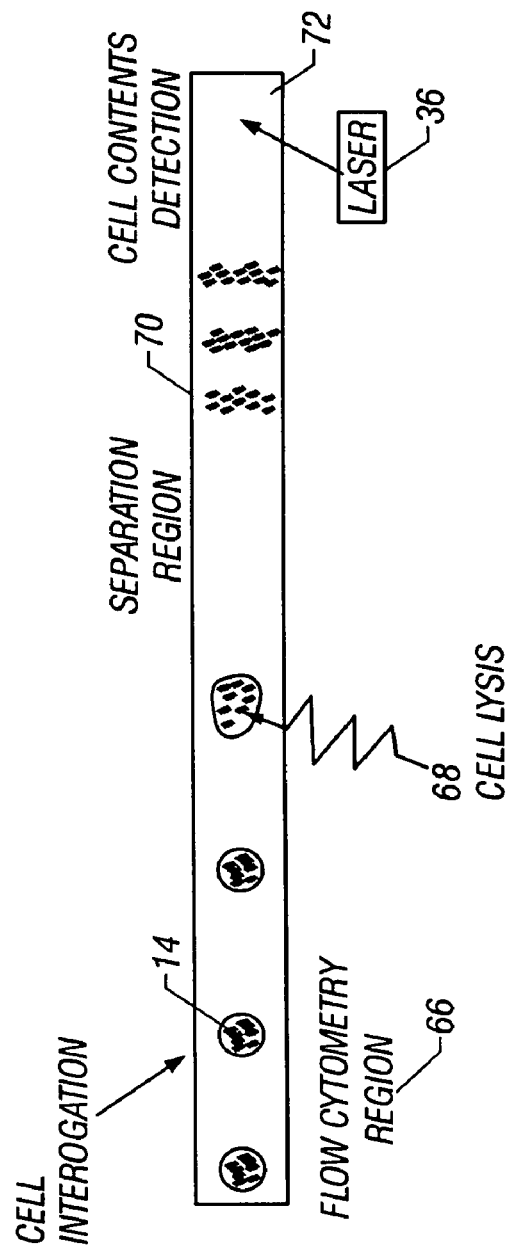
FIG. 13 shows an example as to how flow cytometry (with or without sheath flow) might be combined with the assay.
Figure 14A:
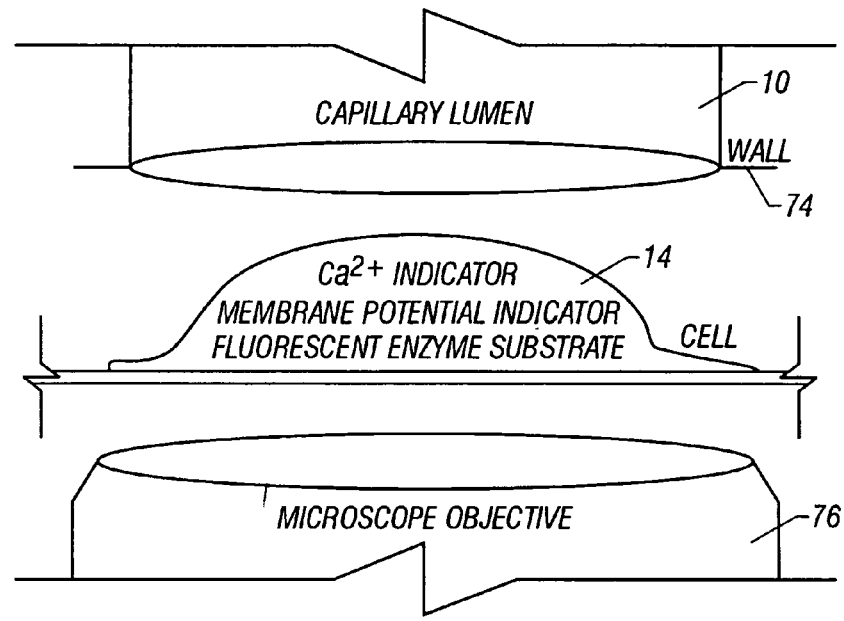
FIG. 14 shows examples as to how fluorescence microscopy or patch clamp techniques might be combined with the assay.
Figure 14B:
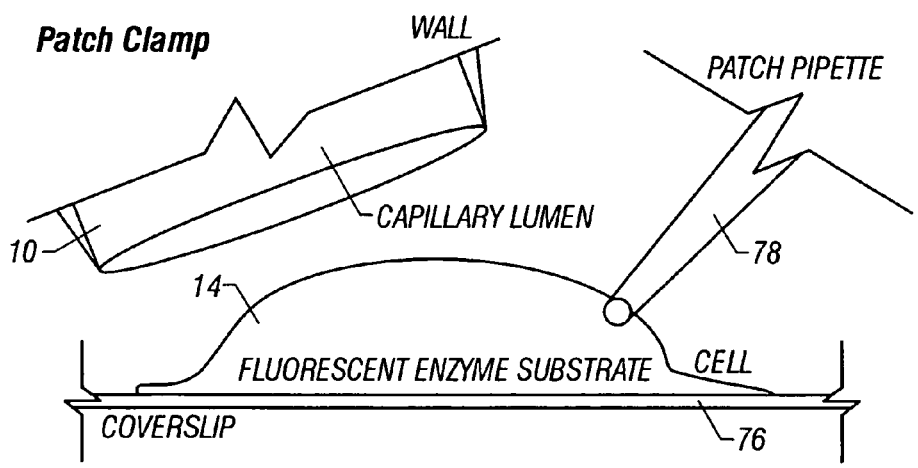

The affinity arrays 52 are preferably, but not limited to, arrays of DNA or proteins. Flow cytometry may also be combined with the described technique for measuring protein activity to increase the rate at which assays are performed. FIG. 13 diagrammatically illustrates analysis by flow cytometry. Cell interrogation is performed on cells 14 in flow cytometry region 66 with cell lysis occurring at 68. The cell contents are electrophoretically separated at 70 and then fluorescently detected at 72 by laser 36. Flow cytometry may be accomplished with sheathed or unsheathed fluid flow. FIG. 14 diagrammatically illustrates how fluorescence microscopy or patch clamp techniques might be combined with the assay. The upper portion of FIG. 14 shows the use of microlumen 10 in a sampling chamber 74 in which a cell 14 with a $Ca^{2+}$ indicator, a membrane potential indicator, or fluorescent enzyme substrate has been loaded and which is then fluorescently imaged through a microscope objective 76. In the lower portion of FIG. 14 microlumen 10 is inserted into chamber 74 in a cell 14 on cover slip 76 which cell 14 has been loaded with a fluorescent enzyme substrate by patch pipette 78.

Figure 15A:
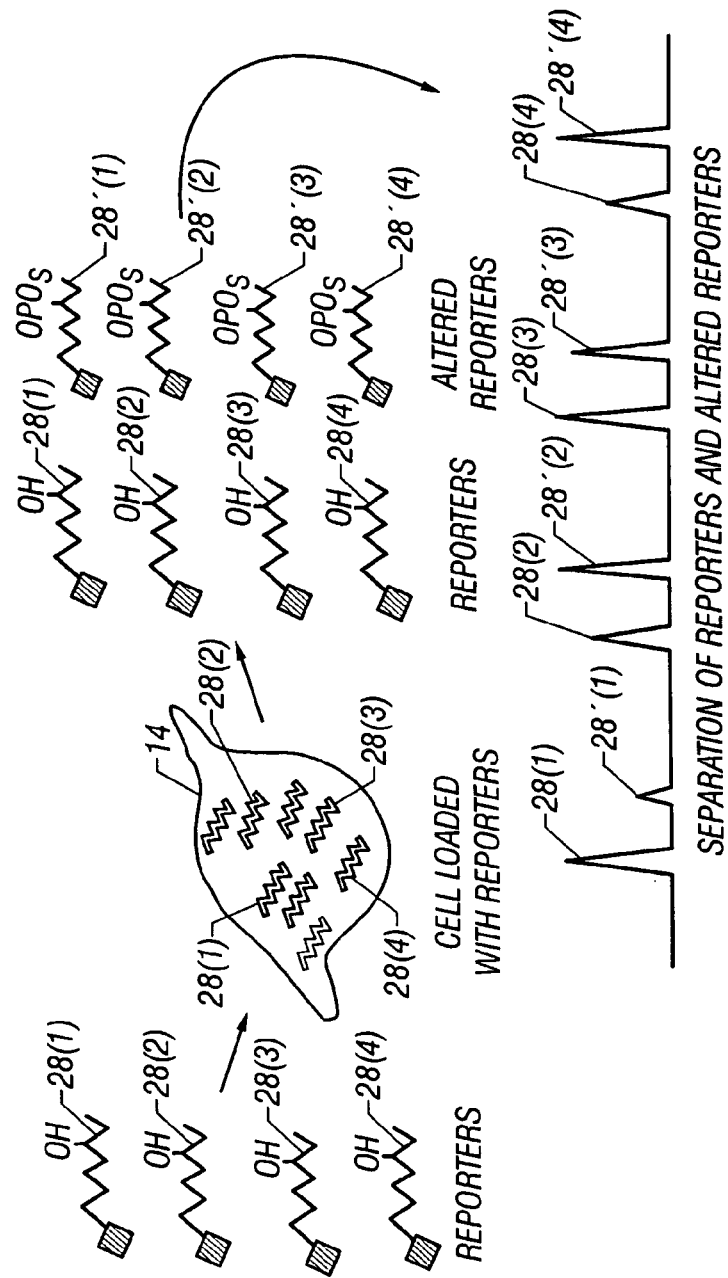
FIG. 15A is a schematic of the measurement of 4 enzymatic activities in a single cell of what is defined in this specification as a "profile of the signal transduction pathways".
Figure 15B:
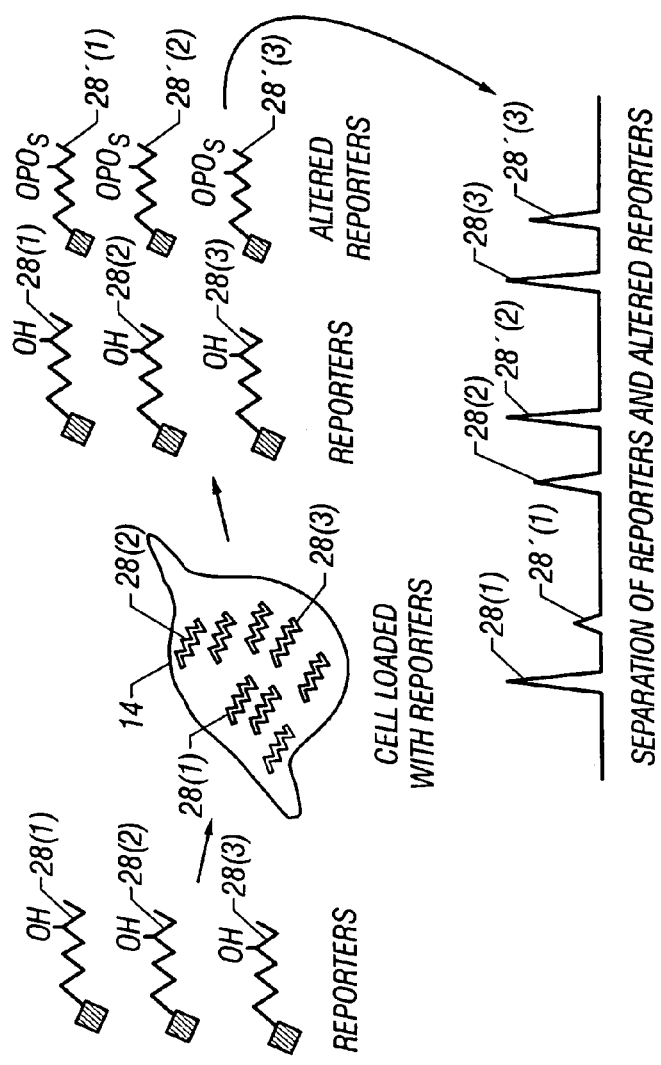
FIG. 15B is a schematic of the profile of the signal transduction pathways or measurement of 3 enzymatic activities in a single cell.
Figure 16:
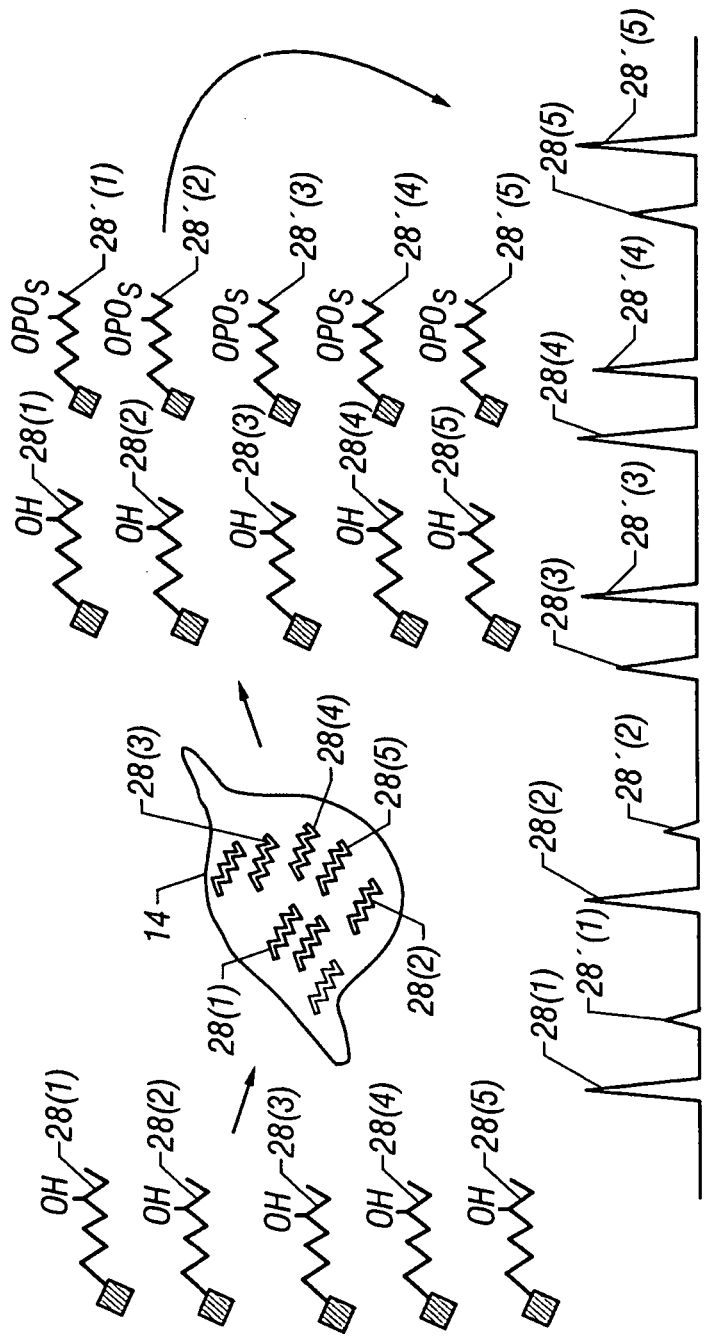
FIG. 16 is a schematic of the profile of the signal transduction pathways or measurement of 5 enzymatic activities in a single cell.
Figure 17:
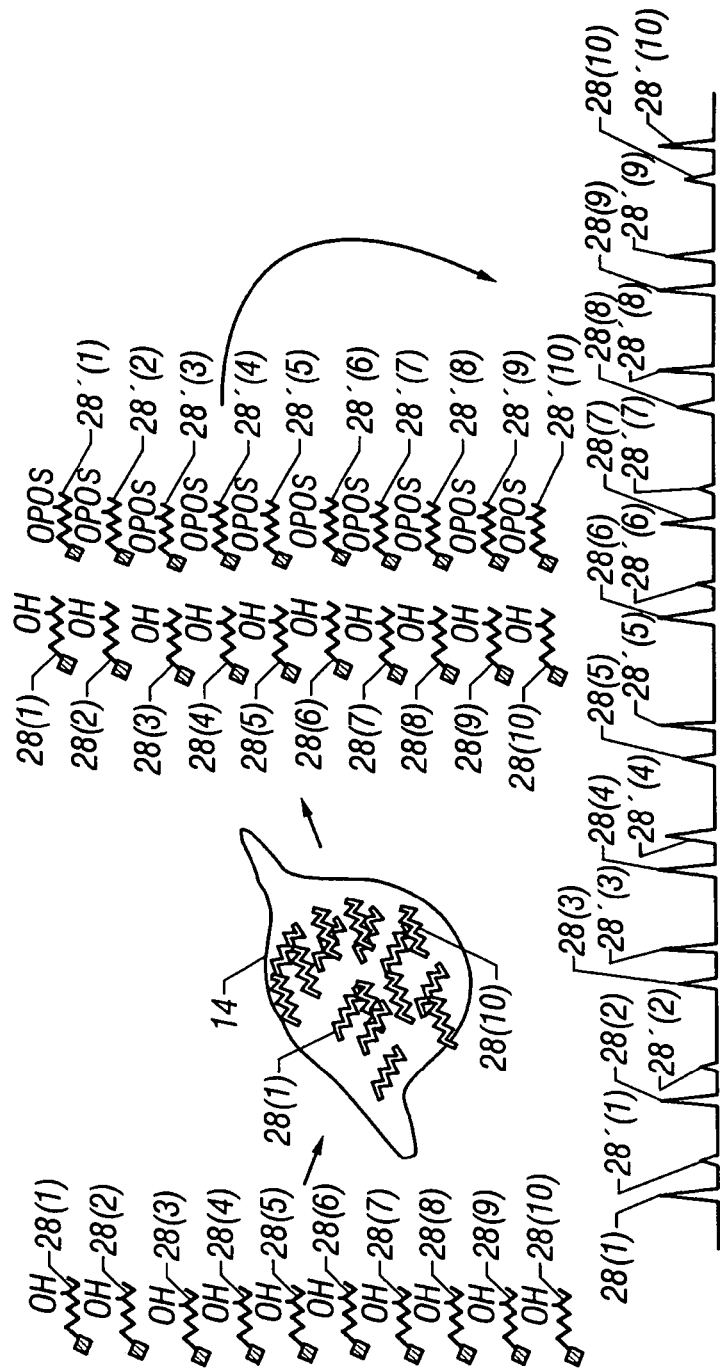
FIG. 17 is a schematic of the profile of the signal transduction pathways or measurement of 10 enzymatic activities in a single cell.

The ability of the technique to analyze multiple enzymes 30 can be exploited to discover networks of functionally interacting enzymes and assess drug selectivity in vivo. Multiple enzymes can be studied by introducing multiple reporters into the cell 14 (FIGS. 15-18). For example, to determine the activity of four enzymes simultaneously in an individual cell 14, portion of a cell 14 or group of cells 14, four reporters are introduced into the cell 14, the reaction is stopped, and the extent to which the reporters are modified is determined as shown in FIG. 15A and B. FIG. 15A is a schematic of what is defined in this specification as a "profile of the signal transduction pathways" or a measurement of four enzymatic activities in a single cell 14. Reports 28(1)–(4) are loaded into cell 14 and then both unaltered reporters 28(1)–(4) and altered reporters 28'(1)–(4) lysed, separated and analyzed to produce four distinct electropherograms showing the relative amounts and existence of unaltered reporters 28(1)–(4) and altered reporters 28'(1)–(4). FIG. 15B is a similar schematic which shows the profile of the signal transduction pathways or measurement of three enzymatic activities relating to unaltered reporters 28(1)–(3) and altered reporters 28'(1)–(3) in a single cell 14. To assess the activity of more than four enzymes simultaneously, additional reporters 29($j$) are introduced for each corresponding enzyme 30 being studied as diagrammatically shown in FIGS. 16–18 where five unaltered reporters 28(1)–(5) and altered reporters 28'(1)–(5) in a single cell 14 are shown in FIG. 16, ten unaltered reporters 28(1)–(10) and altered reporters 28'(1)–(10) in a single cell 14 in FIG. 17 and a multiplicity of unaltered reporters 28(1)–(n) and altered reporters 28'(1)–($n$) in a single cell 14 in FIG. 18. The reporters can be specific for one enzyme 30, or can be substrates for several enzyme 30. In the case of reporters 28 that react with several enzymes 30, the activity of a single enzyme 30 can be determined by introducing a group of reporters 28 with overlapping specificity. For example, reporter 28A interacts with enzymes 30(1), (2), and (3), and reporter 28B interacts with enzymes 30(2), 30(3), and 30(4). Both reporters 28A and B are introduced into the cell 14. If only reporter 28A is modified, then of the enzymes 30($b$)–(4) only enzyme 30(1) is active. If only reporter 28B is modified, then only enzyme 30(4) is active. The response of a cell 14 to a stimulus over a period of time can be determined by loading a group of cells 14 with a reporter or reporters 28, stimulating the group of cells 14, and the examining sub groups of these cells 14 by the described method at defined periods of time.

Figure 18:
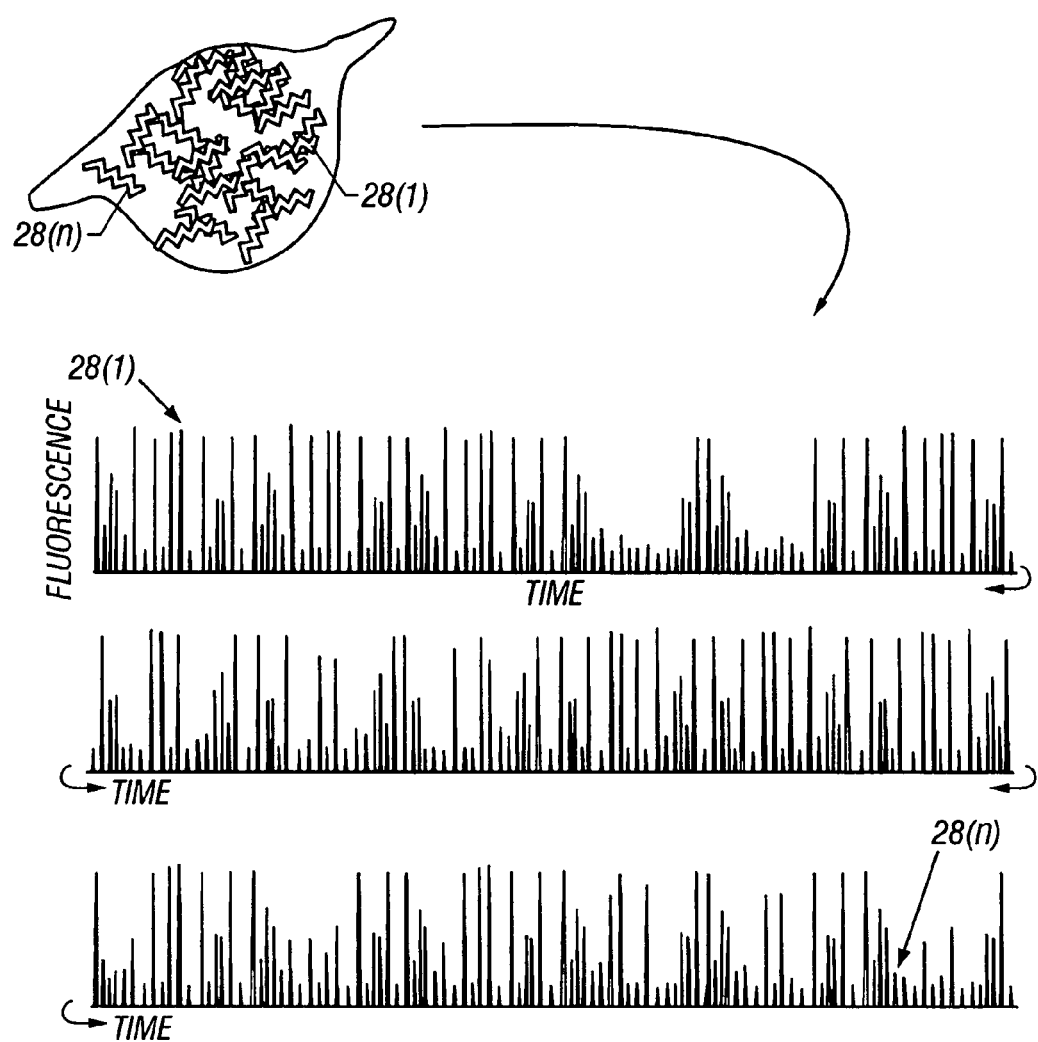
FIG. 18 is a schematic of the measurement of a large number of enzymatic activities in a cell which might be used to "enzymatically fingerprint" a cell thereby producing a profile of the signal transduction pathways. Here various of the reporters might be labeled with fluorescent tags possessing differing spectral characteristics to aid in distinguishing them by virtue of a separation based on their spectral properties rather than their electrophoretic properties.

The described method has the potential to measure the activation state of a large numbers of enzymes 30 simultaneously in the same cell 14, ie. to produce an "enzymatic fingerprint" of a single cell 14, a population of cells 14, or portion of a cell 14 as illustrated diagrammatically for an arbitrary number, n, of enzymes in FIG. 18. Clearly, measurement of the activation status of numerous signal transduction pathways in a single cell 14, a population of cells 14, or portion of a cell 14 will yield an understanding of the roles of normal and abnormal signal transduction pathways in normal and disease states. In addition, enzymes 30 are promising targets for drug therapies, and the development of pharmacologic antagonists is an intense area of research. Determining the number, identities, and degree of activation of involved enzymes 30 in normal and diseased cells 14 will aid in identifying drug targets and in screening for active compounds. In addition to basic cancer biology and pharmaceutical development, the method also has great promise in clinical medicine. Many diseases continue to be categorized by pathologic criteria, yet are known to differ in the molecular basis underlying their phenotype. It is the altered intracellular protein activity rather than histologic appearance that actually drives the different behavior of different disease states. Disease fingerprinting by molecular criteria such as surface receptors or genotype is now recognized as a valuable adjunct to disease classification and therapeutic decisions. However, these measurements still provide only an indirect assessment of which pathways are unregulated. "Enzymatic fingerprinting" of a single cell 14, a population of cells 14, or portion of a cell 14 would provide a direct measure of the signaling pathways involved in a given patient's disease. One could then easily envision individualized chemotherapeutic regimens targeted at the unregulated pathways driving a particular patient's disease.

Figure 19:
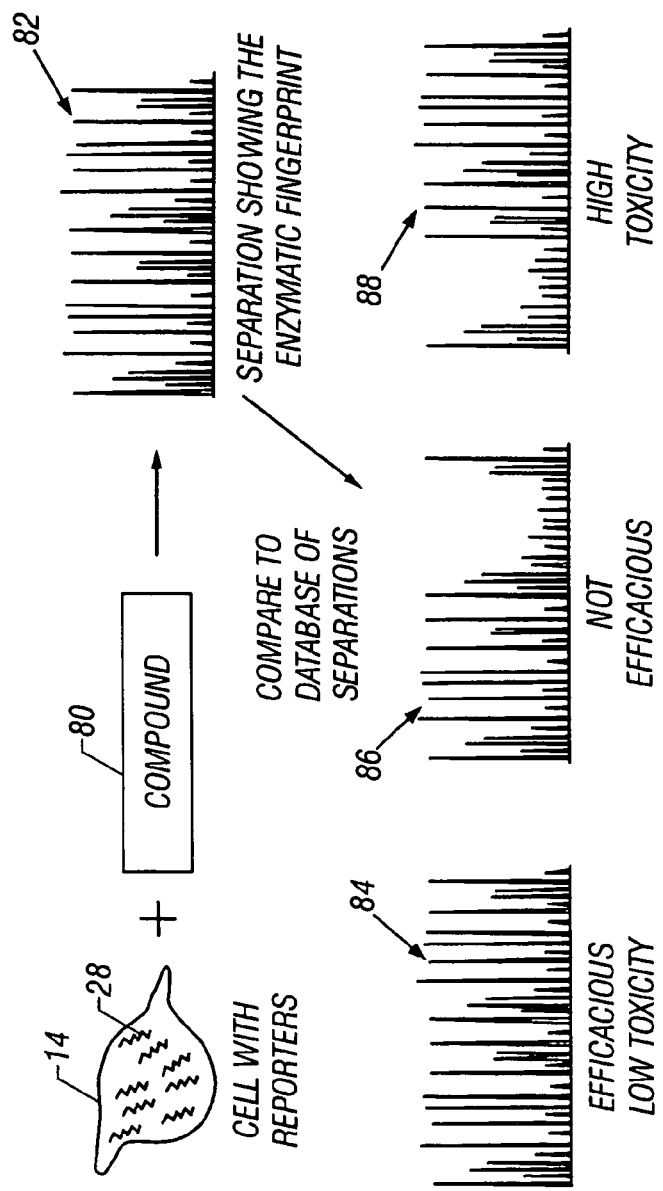
FIG. 19 is a schematic of one way in which the activity profile (or enzymatic fingerprint) obtained from a cell exposed to a compound or drug could be compared to a database of activity profiles created from known drugs or compounds.

Protein activity maps can be produced by analyzing the activities of large numbers of enzymes in the presence or absence of a stimulus in many different types of cells 14. In this way activity profiles of drugs and potential drugs can be assessed as diagrammatically shown in FIG. 19. Loaded cell 14 is treated with a compound or drug of interest 80 from which an electropherogram 82 is obtained, which provides a enzymatic fingerprint such as discussed in FIG. 18. This enzymatic fingerprint of electropherogram 82 is then compared to a database of separation electropherograms which include enzymatic fingerprints of multiple enzymatic pathways where one or more desired enzymatic pathways were affected efficaciously with low toxicity as shown by electropherogram 84, were not efficaciously affected as shown by electropherogram 86, or were affected with high toxicity as shown by electropherogram 88. Efficacious affect may include either promotion or inhibition of one or more enzymatic pathways depending on what is desired in the application at hand.

Figure 20:
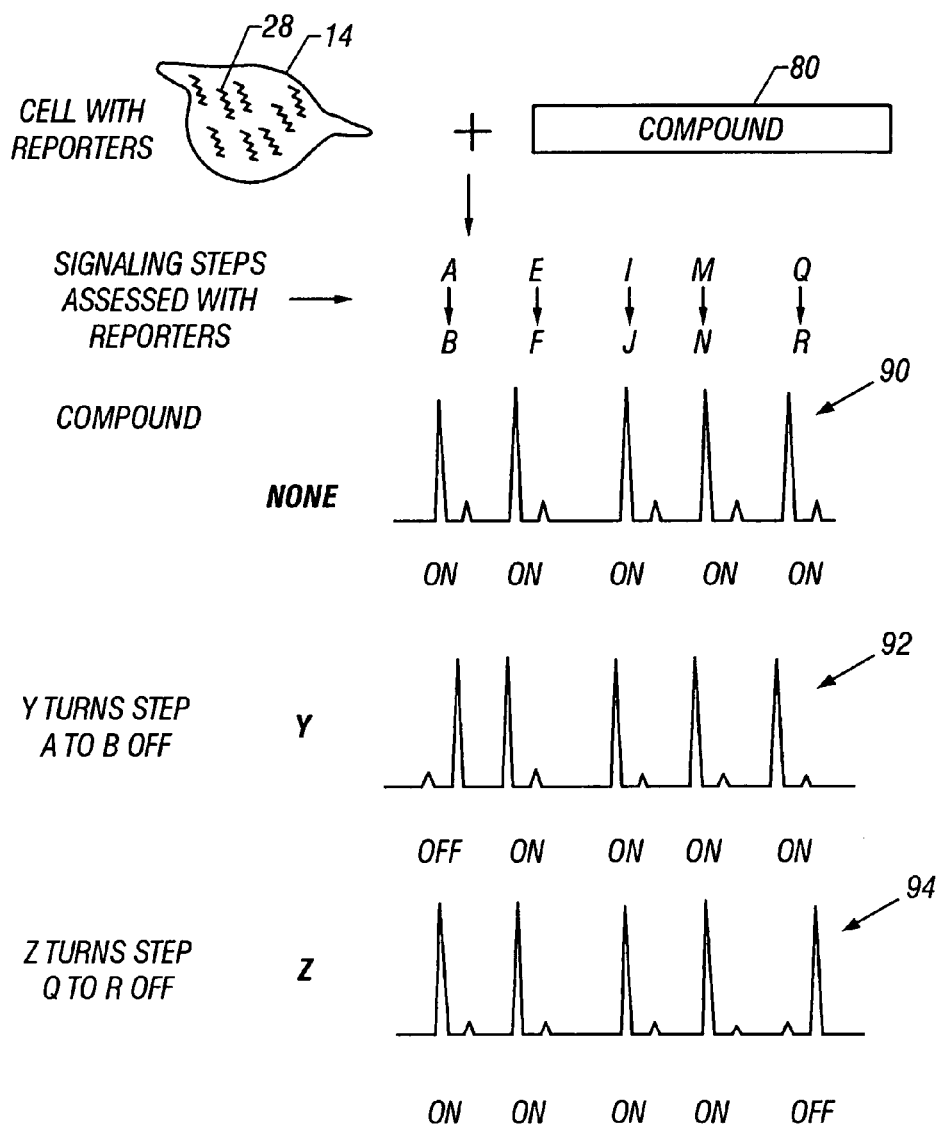
FIG. 20 depicts an example as to how the target of a drug can be identified by loading cells with a mixture of reporters representing enzymatic steps that might be inhibited by a drug or compound.
Figure 21:
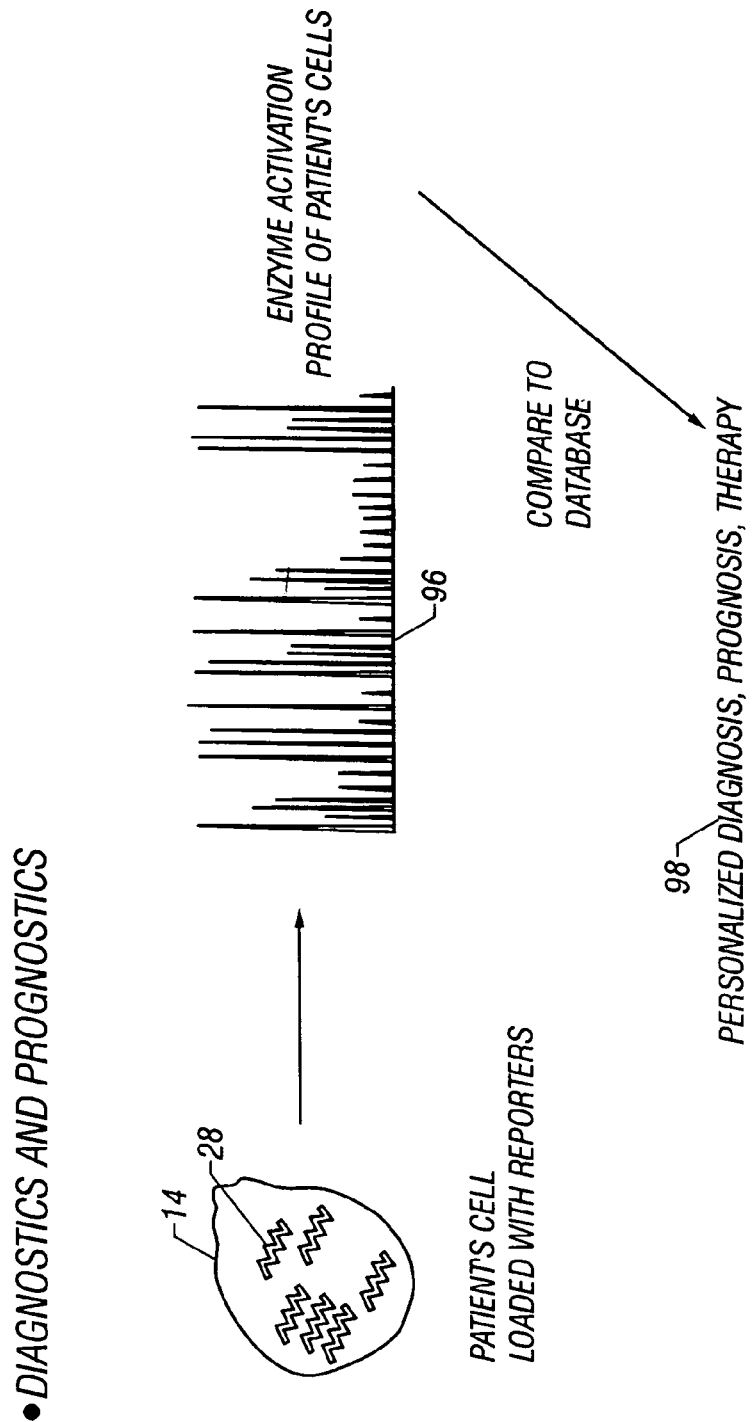
FIG. 21 is an example as to how personalized diagnosis, prognosis, and or therapy can be performed by loading reporter molecules into a patient's cell(s).
Figure 22:
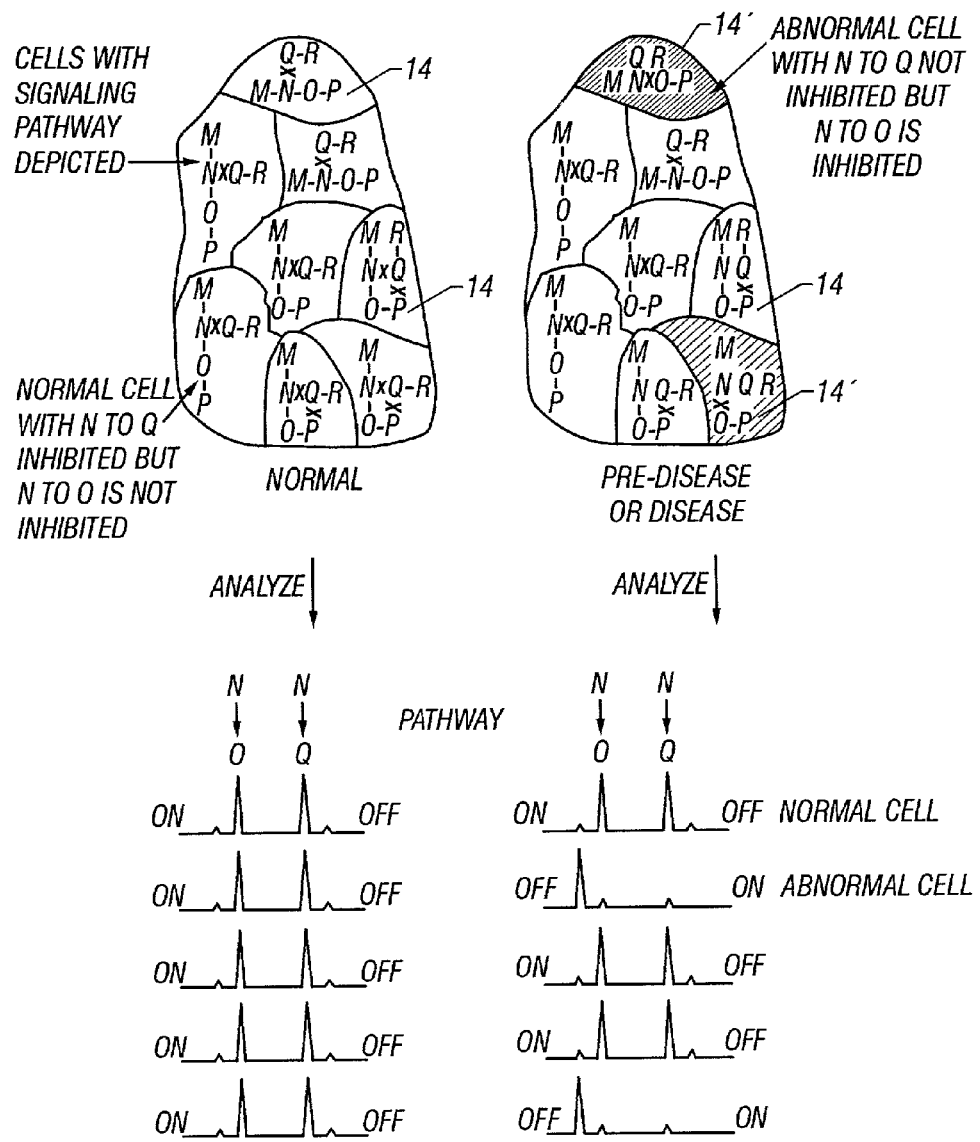
FIG. 22 is a schematic showing how disease or predisease states can be distinguished from a normal state by loading reporter molecules into cells and comparing enzymatic profiles.

Cellular targets of compounds (for example, but not limited to, toxicity testing) can also be identified as depicted in FIG. 20. Cell 14 loaded with reporters 28 are again treated in any manner now known or later devised with a compound or substance of interest 80. Assume reporters 28 related to signaling steps A to B, E to F, I to J, M to N and Q to R where the letters represent various biochemical pathways of interest. Where compound 80 had not affect on the signaling steps, an electropherogram 90 might be known in included in the database. In the case where enzyme Y turns step A to B off, an electropherogram 92 is obtained. In the case where enzyme Z turns step Q to R off, an electropherogram 94 is obtained. The activity profile of drugs with known negative side effects can be determined by this method and used to screen new drug candidates for the same negative side effects before the compound is used in animal or human studies. As new drugs are examined and new reporters 28 are developed, a new activity map can be assembled by adding newly discovered relationships to the previously assembled database. Similarly protein activity maps can be used to identify and categorize disease or predisease states. These protein activity maps are then useful for diagnosis, prognosis, and therapeutic planning for patients as diagrammatically depicted in FIGS. 21 and 22. In FIG. 21 a cell sample is taken from a specific patient and loaded with selected reporters 28. An electropherogram 96 is obtained as an enzymatic fingerprint for that patient. This enzymatic fingerprint is then compared to enzymatic fingerprints in the database to diagnosis the patient or provide a prognosis of a therapy which has been applied to the patient. FIG. 22 illustrates the method in the case of multiple cells to find normalcy or diseased conditions. Again cell samples are taken. In the left of FIG. 22 seven cells 14 are shown, all of which are normal. For example a normal cell 14 may have signaling pathways N to Q inhibited and N to O not inhibited. On the left of FIG. 22 is a sample of seven cells 14 in which two cells 14' are in a pre-diseased or diseased state. In pre-diseased or diseased cells 14' the signaling pathway N to Q is not inhibited and N to O is inhibited. Both samples are analyzed according to the invention the series of electropherograms of the N to O and N to Q signaling pathways for the separate cells are obtained as shown in the bottom of FIG. 22. These electropherograms will of course be merged in a multiple cell analysis. On the left there are contributions only from normal cells, but on the right the two pre-diseased or diseased cells 14' contributing. Since the activity maps identify pathways and proteins which participate directly or indirectly in causing disease, the maps can also be used to identify new drug targets.

Figure 23:
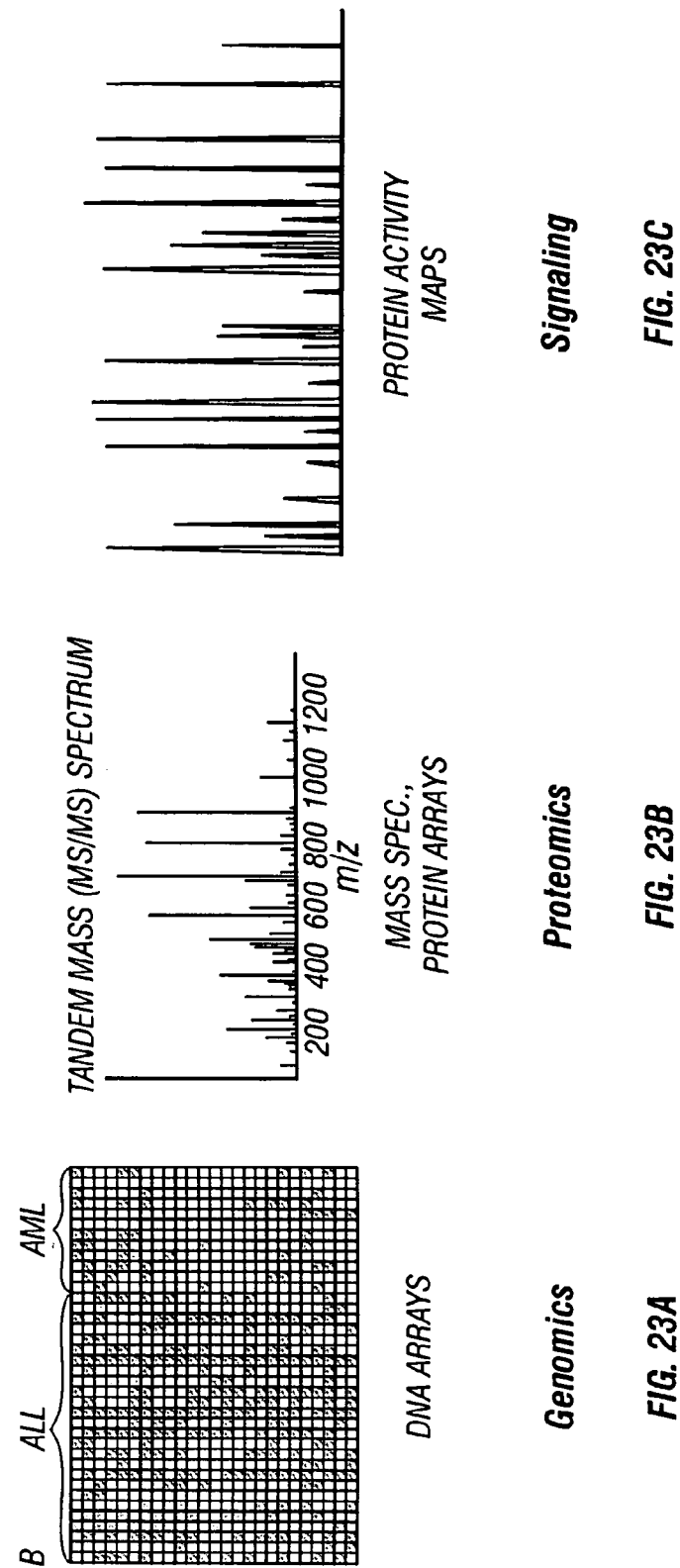
FIG. 23 depicts the parallels between genomics, proteomics and signaling, and the expectation that the applications for enzyme activity maps will be comparable to those currently in use or envisioned for genomics and proteomics technologies.

These protein activity maps will be used in much the same way as other highly parallel mapping technologies such as DNA arrays, two dimensional-gels/mass spectroscopy, and protein arrays as illustrated symbolically in FIG. 23 and in Table III. However, rather than measuring quantitatively RNA or protein identity/concentration, the method of the invention will measure protein activity (FIG. 23 and Table II). Applications of the method of the invention will be much the same as for DNA arrays, protein arrays and mass spectroscopy. Analysis of protein activity maps as a database will be an important approach for analysis of biological systems. The use of protein activity maps as a data archive will identify all of the protein activities in various cells 14 under all possible conditions. These applications include, but are not limited to, characterization of metabolic pathways, characterization of regulatory pathways, characterization of diseased and normal tissues, identification of drug targets, establishment of the mechanism of action of drugs and toxic agents. Databases of protein activity maps can be coupled to databases of mRNA expression, protein identity/concentration and other databases for a fuller understanding of biologic processes.

Figure 24:
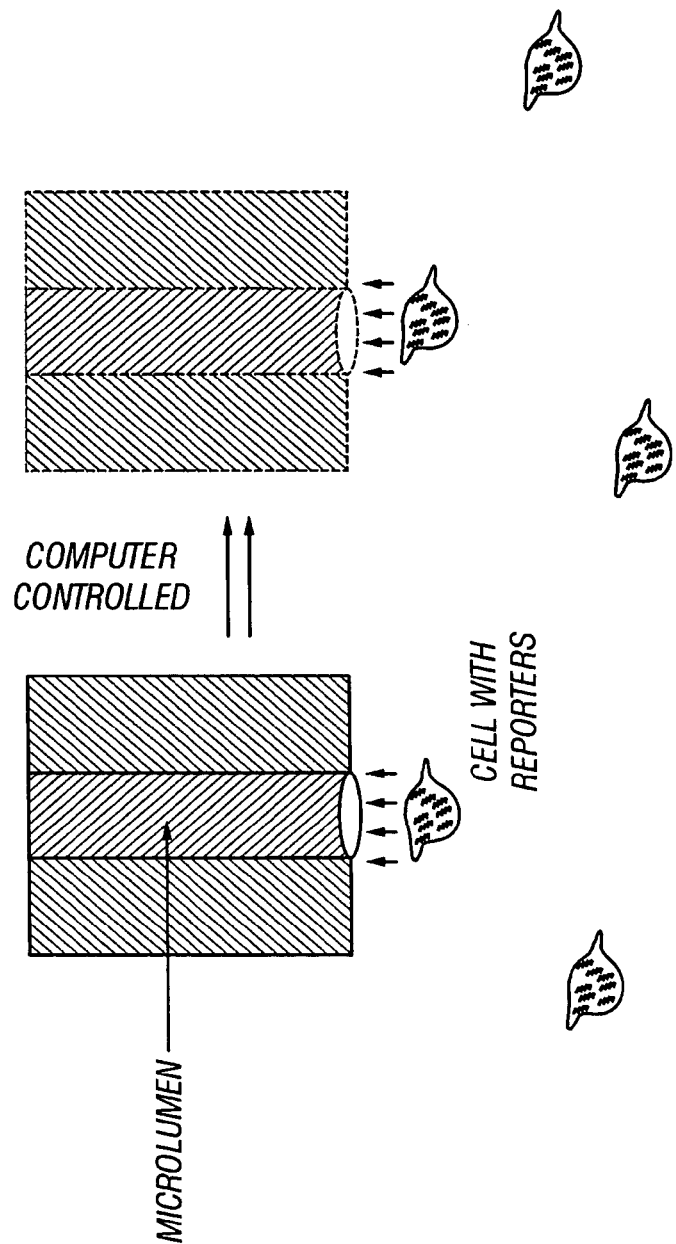
FIG. 24 depicts the computer-controlled identification and selection of cells for analysis and computer control of the movement of the cells or of the microlumen.
Figure 25:
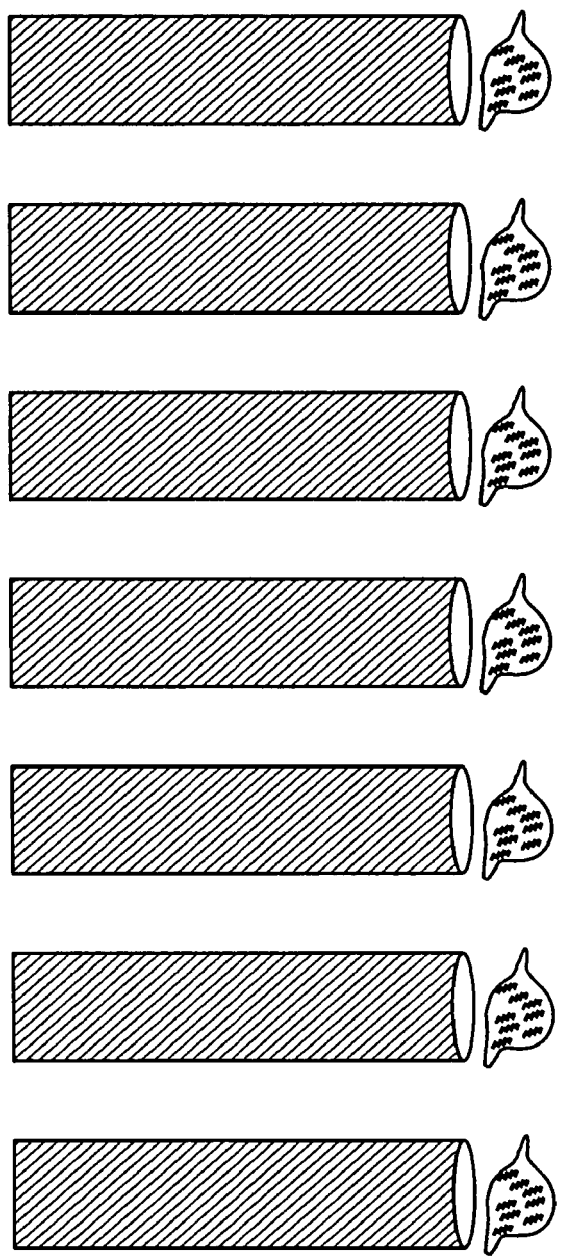
FIG. 25 is a schematic of a computer-controlled array of microlumens positioned over an array of cells loaded with reporter molecules for the highly parallel analysis of many cells. A microfabricated array of channels might also be utilized.

The steps described in the method to simultaneously examine the activity of multiple enzymes in a single living cell 14, portion of a cell 14, or in a group of cells 14 may individually or in combination be controlled by a computer. For example, but not limited to, the cell locating device, the collection device, the separation device, the cell lysing device, and the reporter detecting device can all be computer-controlled. Computer control of the various assay steps can be used alone or in combination with other techniques to increase the throughput rate of the method to simultaneously examine the activity of multiple enzymes in cell(s) 14. These other techniques include, but are not limited to, placing cells 14 on array 52 by manipulating the surface properties of the array and multiplexed serial or parallel analyses of cells 14 such as diagrammatically depicted in FIG. 24 and 25. FIG. 24 contemplates that either the cells 14 or microlumen 10 will be moved relative to each other by computer controlled electromechanical devices to make a serial assay. FIG. 25 assumes that multiple microlumens 10 form multiple channels for making simultaneous or parallel assays of multiple cells 14. Also included are computer-automated microchip-based strategies as was shown in FIG. 12B, and informatics technologies to distinguish and identify large numbers of peaks on the electropherograms as discussed in connection with FIG. 18.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in must be understood as being generic to all possible meanings supported by the specification and by the word itself.

The definitions of the words or elements of the following invention and its various embodiments are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the invention and its various embodiments below or that a single element may be substituted for two or more elements in a claim.

Insubstantial changes from the claimed subject matter as viewed by a person with ordinary skill in the art, now known or later devised, are expressly contemplated as being equivalently within the scope of the invention and its various embodiments. Therefore, obvious substitutions now or later known to one with ordinary skill in the art are defined to be within the scope of the defined elements.

The invention and its various embodiments are thus to be understood to include what is specifically illustrated and described above, what is conceptionally equivalent, what can be obviously substituted and also what essentially incorporates the essential idea of the invention.

TABLE I

Influence of the Intracellular Environment

| Cellular Property | Is it the same after removal from the cell? |
|---|---|
| 1. DNA, RNA (sequence, quantity) | Yes |
| 2. Protein (identity, conc.) | Likely |
| 3. Activity | Usually Not |

TABLE II

Cellular Properties Are Distinguished By Their Timescales

| | |
|---|---|
| DNA & RNA "Genomics" | Minutes-Years |
| Protein "Proteomics" | Seconds-Hours |
| Activity "Signaling" | Milliseconds-Seconds |

TABLE III

A Sampling Of Available Technologies

| Field | Property | Technologies |
|---|---|---|
| 1. Genomics | DNA, RNA | DNA Arrays |
| 2. Proteomics | Protein Identity & Conc. | Protein Gels/Arrays Mass Spec. |
| 3. Signaling | Activity | GFP-Based Methods Critical Need |

We claim:

1. A method of detecting activities of a plurality of different enzymes in a cell, comprising:
   introducing reporter molecules into the cell;
   releasing the reporter molecules from the cell; and
   detecting the reporter molecules to detect the activities of the plurality of different enzymes in the cell,
   wherein the plurality of different enzymes comprises at least four enzymes.

2. The method of claim 1, wherein the reporter molecules comprise at least one member selected from the group consisting of unaltered reporter molecules and altered reporter molecules.

3. The method of claim 1, further comprising recording and tabulating the activities of the plurality of enzymes.

4. The method of claim 1, further comprising exposing the cell to an external stimulus.

5. The method of claim 4, wherein the external stimulus comprises a compound.

6. The method of claim 5, wherein the compound is a polypeptide.

7. The method of claim 5, further comprising recording and tabulating the activities of the plurality of enzymes, and further comprising compiling a map of cellular responses to the compound.

8. The method of claim 1, wherein an auxiliary molecule that enters the cell is attached to at least one reporter molecule.

9. The method of claim 8, wherein the auxiliary molecule is selected from the group consisting of a peptide and a peptide analog.

10. The method of claim 1, wherein at least one reporter molecule comprises a label.

11. The method of claim 10, wherein the label is selected from the group consisting of a fluorescent group, a stable isotope, a radioactive isotope, and biotin.

12. The method of claim 10, wherein a first reporter molecule comprises a first label, and a second reporter molecule comprises a second label that is different than the first label.

13. The method of claim 1, further comprising stopping reactions between the reporter molecules and the enzymes after releasing the reporter molecules.

14. The method of claim 13, wherein the time between releasing the reporter molecules and stopping the reactions is less than 1 second.

15. The method of claim 14, wherein the time is less than 33 milliseconds.

16. The method of claim 15, wherein the time is less than 10 microseconds.

17. The method of claim 1, wherein detecting further comprises separating the reporter molecules using at least one technique selected from the group consisting of electrophoresis, two-dimensional gel electrophoresis, microchromatography and flow cytometry.

18. The method of claim 1, wherein detecting comprises using at least one technique selected from the group consisting of mass spectroscopy, fluorescence polarization spectroscopy, flow cytometry, yeast two-hybrid assay, morphological analysis, intercellular ion indicator activity, protein localization and affinity arrays.

19. The method of claim 1, wherein detecting comprises detecting the reporter molecules on a microfluidics device.

20. The method of claim 1, wherein detecting further comprises separating the reporter molecules on a microfluidics device.

21. The method of claim 1, wherein the plurality of different enzymes comprises at least five enzymes.

22. The method of claim 1, wherein the plurality of different enzymes comprises at least six enzymes.

23. The method of claim 1, wherein the plurality of different enzymes comprises at least ten enzymes.

24. The method of claim 1, wherein the cell comprises a portion of a cell.

25. The method of claim 1, wherein the introducing comprises introducing at least one of the reporter molecules at a concentration of at most 10 micromolar.

26. The method of claim 1, wherein the introducing comprises introducing at least one of the reporter molecules at a concentration of at most 1 micromolar.

27. The method of claim 1, wherein the introducing comprises introducing at least one of the reporter molecules at a concentration of at most 100 nanomolar.

28. The method of claim 1, further comprising diminishing or terminating a chemical reaction involving the reporter molecules using scavengers or inhibitors.

29. The method of claim 1, further comprising labeling the reporter molecules and stopping a chemical reaction involving the reporter molecules by introducing an unlabeled reporter molecule.

30. The method of claim 1, further comprising stopping a chemical reaction involving the reporter molecules before releasing the reporter molecules and unaltered reporter molecules from the cell.

31. The method of claim 28, wherein the diminishing or terminating comprises photochemically introducing the scavenger or inhibitor from a caged scavenger or caged inhibitor.

32. The method of claim 1, wherein detecting comprises quantifying the activities of at least three enzymes.

33. The method of claim 1, wherein detecting comprises quantifying the activities of at least ten enzymes.

* * * * *